US008614303B2

(12) United States Patent
Madura et al.

(10) Patent No.: US 8,614,303 B2
(45) Date of Patent: Dec. 24, 2013

(54) DIAGNOSTIC METHODS FOR UBIQUINATED PROTEIN PROFILING

(75) Inventors: Kiran Madura, Bridgewater, NJ (US); Li Chen, Hillsboro, NJ (US)

(73) Assignee: University of Medicine and Dentistry, Somerset, NJ (US)

( * ) Notice: Subject to any disclaimer, the term of this patent is extended or adjusted under 35 U.S.C. 154(b) by 800 days.

(21) Appl. No.: 10/498,068

(22) PCT Filed: Dec. 11, 2002

(86) PCT No.: PCT/US02/39683
§ 371 (c)(1),
(2), (4) Date: Jun. 16, 2005

(87) PCT Pub. No.: WO03/049602
PCT Pub. Date: Jun. 19, 2003

(65) Prior Publication Data
US 2005/0287608 A1    Dec. 29, 2005

Related U.S. Application Data

(60) Provisional application No. 60/339,543, filed on Dec. 11, 2001.

(51) Int. Cl.
C07K 1/22      (2006.01)
B01D 15/38     (2006.01)
G01N 33/566    (2006.01)
G01N 30/02     (2006.01)

(52) U.S. Cl.
USPC ............................ 530/413; 435/7.1; 436/161

(58) Field of Classification Search
None
See application file for complete search history.

(56) References Cited

U.S. PATENT DOCUMENTS

| 4,281,061 | A  |   | 7/1981  | Zuk et al. |   |
|---|---|---|---|---|---|
| 4,355,023 | A | * | 10/1982 | Ehrlich et al. | 530/387.3 |
| 4,490,472 | A | * | 12/1984 | Gottlieb | 536/24.31 |
| 5,047,509 | A | * | 9/1991  | Silvestrini et al. | 530/392 |
| 5,206,347 | A | * | 4/1993  | Ruoslahti et al. | 530/413 |
| 5,538,897 | A |   | 7/1996  | Yates et al. | 436/89 |
| 5,876,691 | A | * | 3/1999  | Chester et al. | 424/1.49 |
| 6,329,171 | B1| * | 12/2001 | Kapeller-Libermann | 435/69.1 |
| 6,818,411 | B2| * | 11/2004 | Hutchens et al. | 435/7.2 |
| 7,183,116 | B2| * | 2/2007  | Aebersold et al. | 436/86 |
| 7,524,635 | B2| * | 4/2009  | Buechler | 435/7.1 |

FOREIGN PATENT DOCUMENTS

| WO | WO 91/09311  |   | 6/1991  | ............. G01N 33/53 |
|---|---|---|---|---|
| WO | WO 98/57978  | * | 12/1998 | ............. C07K 1/22 |
| WO | WO99/35502   |   | 7/1999  |  |
| WO | WO 00/09654  |   | 2/2000  |  |
| WO | WO 01/27624  |   | 4/2001  |  |
| WO | WO 01/64837  |   | 9/2001  |  |
| WO | WO 01/68664  |   | 9/2001  |  |

OTHER PUBLICATIONS

Layfield et al. "Purification of poly-ubiquitinated proteins by S5a-affinity chromatography" Proteomics vol. 1, Issue 6, pp. 773-777 Published Online: Jun. 27, 2001.*
Bertolaet et al. ("UBA domains of DNA damage-inducible proteins interact with ubiquitin" Nat Struct Biol. May 2001;8(5):417-22.*
Chen et al. "Ubiquitin-associated (UBA) domains in Rad23 bind ubiquitin and promote inhibition of multi-ubiquitin chain assembly" EMBO Rep. Oct. 2001;2(10):933-8. Epub Sep. 24, 2001).*
Rachubinski et al., The p56$^{lck}$—interacting Protein p62 Stimulates Transcription via the SV40 Enhancer, *Journal of Biological Chemistry*, 274: 18278-18284 (1999).
Chen et al., Rad23 Promotes the Targeting of Proteolytic Substrates to the Proteasome, Molecular and Cellular Biology, 22:4902-4913 (2002).
Raasi et al., Binding of Polyubiquitin Chains to Ubiquitin-associated (UBA) Domains of HHR23A, J. Mol. Biol, 341:1367-1379 (2004).
Pickart, Ubiquitin in chains, TIBS, 25:544-548 (2000).
Pickart et al., Ubiquitin: structures, functions, mechanisms, Biochimica et Biophysica Acta, 1695:55-72 (2004).
Thrower et al., Recognition of the polyubiquitin proteolytic signal, The EMBO Journal, 19:94-102 (2000).
C. Wilkinson et al., Proteins Containing the UBA Domain Are Able to Bind to Multi-ubiquitin Chains, Nat. Cell Biol., 2001, 3:939-943.
H. Hiyama et al., "Interaction of hHR23 with S5a", J. Biol. Chem., 1999, 274:28019-28025.
D. Lambertson et al., "Pleiotropic Defects Caused by Loss of the Proteasome-Interacting Factors Rad23 and Rpn10 of *Saccharomyces cerevisiae*," Genetics 1999, 153:69-79.
S. van Nocker et al., "The Multiubiquitin-Chain-Binding Protein Mcb1 Is a Component of the 26S Proteasome in *Saccharomyces cerevisiae* and Plays a Nonessential, Substrate-Specific Role in Protein Turnover", Mol. Cell Biol., 1996:16:6020-6028.
Y. Kimura et al., "Proteomic Analysis of Post-Translationally Modifications of Proteasome", Jpn. J. Electroph., 2001:45:129, Summary/abstract only.

* cited by examiner

*Primary Examiner* — Christine Foster
(74) *Attorney, Agent, or Firm* — Licata & Tyrrell, P.C.

(57) ABSTRACT

Methods for establishing a protein expression profile of a biological sample, by contacting a biological sample with a ubiquitin-binding protein such that ubiquitinated and specific non-ubiquitinated protein (the IPS) bind to the ubiquitin-binding protein; isolating the IPS proteins; and analyzing the isolated IPS proteins, wherein an expression profile is generated.

7 Claims, 9 Drawing Sheets

Yeast        Human

Rad23  hR23-A  hR23-B

UBA1  UBA2  UBA1  UBA2  UBA1  UBA2

Purification and resolution of
Rad23-bound proteins

DIAGNOSTIC METHODS FOR UBIQUINATED PROTEIN PROFILING

CROSS REFERENCE TO RELATED APPLICATIONS

The present application is a National Stage Application claiming the priority of co-pending PCT Application No. PCT/US02/39683, filed Dec. 11, 2002, which in turn, claims priority from United States Provisional Application 60/339, 543, filed Dec. 11, 2001. Applicants claim the benefits of 35 U.S.C. §120 as to the PCT application and priority under 35 U.S.C. §119 as to the U.S. Provisional application, and the entire disclosures of each of these applications is incorporated herein by reference in its entirety.

GOVERNMENT SUPPORT

The research leading to the present invention was supported in part by Public Health Service grant CA-83875 from the National Cancer Institute. The U.S. government may have certain rights in this invention.

FIELD OF THE INVENTION

This invention relates to methods for obtaining an expression profile for a key set of important cellular proteins (Indicator Protein Set or subset), and the use of protein profiles generated to diagnose the presence of aberrant or pathological conditions. The invention further provides methods for screening therapeutic compounds capable of altering the expression profile of an Indicator Protein Set. The invention also provides the means to specifically determine if a protein of interest is a target of the ubiquitin/proteasome pathway.

BACKGROUND

The study of the protein complement of an organism, termed proteomics, has emerged as an important approach for identifying drug targets and new drugs. The field of proteomics includes two approaches: expression proteomics, which studies global changes in protein expression, and cell-map proteomics, the systematic study of protein-protein interactions (Blackstock et al. (1999) Trends in Biotechnology 17:121-127). Unlike the fixed genome, the proteome is a dynamic entity reflecting gene expression, stability and post-translational alterations. The proteome may be cell or tissue specific, and be affected by the metabolic state, health, and environment of the organism.

Current methods for monitoring global gene expression primarily rely on gene-chip/DNA microarray technology. Another approach for studying the expression of proteins in a cell entails the use of high-resolution 2-dimensional (2D) gel electrophoresis.

Ubiquitin (Ub) is a 76 amino acid protein that is highly conserved in eukaryotes, and is covalently linked to other proteins to mark them for degradation by a protease called the proteasome. Non-proteolytic effects of protein ubiquitination have also been described. Rad23 is a highly conserved protein involved in nucleotide excision repair. Human Rad23 contain amino-terminal ubiquitin-like (UbL) domains that &an bind the proteasome (Schauber et al. (1998) Nature 391:715-718).

BRIEF SUMMARY OF THE INVENTION

The instant invention provides new diagnostic methods for determining the presence of aberrant or pathological conditions in a cell, such as occurring in the presence of disease onset or in transition from normal to transformed or abnormal states. The invention provide a method of establishing an expression profile for a key subset of cellular proteins which are most likely to be altered under different physiological states or conditions. In the method of the invention, the bulk of cellular proteins, which are typically uninformative, is eliminated and the analysis is confined to a small set of the proteins having high predictive value in the diagnosis of cellular abnormalities. The method of the invention is termed "Protein Profiling", and the subset of key cellular proteins which are examined for variation from normal expression are termed the "Indicator Protein Set" ("IPS"). The IPS includes both ubiquitinated and non-ubiquitinated regulatory proteins.

The method of the invention is based, in part, on the realization that the ability of ubiquitin binding proteins, such as Rad23, to bind key cellular proteins can be used diagnostically. An important feature of the methods of the invention is the ability to isolate a specific cohort of cellular proteins that represent important regulators of cell growth and development. Since the levels of this class of proteins are typically altered in aberrant cells, they represent a set of proteins with high diagnostic value.

The methodology described below provides methods for efficiently recovering ubiquitinated and non-ubiquitinated cellular proteins (IPS), determining the expression profile of the IPS, and comparing that the normal expression profile, such that alterations in the IPS profile indicate the presence of aberrant or pathological conditions.

Accordingly, in a first aspect, the invention features a method for establishing an expression profile, or fingerprint, for a tissue or cell, comprising (a) contacting a biological sample with a ubiquitin-binding protein, such that the IPS bind to the ubiquitin-binding protein; (b) isolating the IPS proteins; and (c) analyzing the isolated IPS proteins, wherein an expression profile of IPS proteins for the tissue or cell is established.

The protein profiling method of the invention is used to establish fingerprints for control and disease or pathological samples. In specific embodiments, the biological sample is a control, tumor, or pathological biological sample is any biological sample containing cells or proteins, including peripheral blood, body fluids, tissue biopsy, stool sample, cultured cells, and protein extracts from any source. Very small amounts of cellular materials are required, for example, typically about 0.1 g of biopsy tissue or less, is sufficient for the protein profiling method of the instant invention. With further refinements to the technique, it is envisioned that as little as 1-2 mg of tissue would be sufficient for the protein profiling of the instant application.

In one embodiment, the ubiquitin-binding protein is any natural or artificial protein exhibiting high-affinity binding to ubiquitin. In more specific embodiment, the ubiquitin-binding protein is a natural or artificial peptide construct comprising tandemly-linked ubiquitin-associated (UBA) domains. In another specific embodiment, the ubiquitin-binding protein is Rad23, Ddi11, Dsk2, Rpn10, or ataxin-3. In another specific embodiment, the ubiquitin-binding protein is an anti-ubiquitin antibody. In a more specific embodiment, the anti-ubiquitin antibody is a polyclonal or a monoclonal antibody. These antibodies may be generated against the intact protein, or against synthetic peptides that represent amino acid sequences that are present within the protein of interest.

In a more specific embodiment, the isolating step (b) is conducted by attaching the ubiquitin-binding protein to an affinity matrix, capturing IPS proteins from the biological sample, followed by release of the bound proteins by subjecting them to a de-ubiquitination reaction, and release of non-ubiquitinated proteins by treatment with high salt or other treatments.

In a more specific embodiment, the analyzing step (c) is conducted by subjecting the isolated de-ubiquitinated proteins to high-resolution 2-dimensional gel electrophoresis, wherein a protein profile is obtained specific for that biological sample.

In one specific embodiment, the method is used to generate a protein profile for ubiquitinated and non-ubiquitinated proteins by applying a cell or tissue extract to an affinity column in which recombinant Rad23 expressed as a fusion to glutathione S-transferaseis attached to glutathione-SEPHAROSE®. The bound proteins are dissociated from the column and subjected to resolution by gel electrophoresis. In more specific embodiments, the disassociation of the bound proteins from the affinity column is by high salt conditions, exposure to detergent, SDS, and the like, or with the use of an enzyme able to dissociate the bound proteins from the column, e.g., ubiquitin-isopeptidase. The highly enriched isolated de-ubiquitinated proteins and other cellular non-ubiquitinated proteins, termed the IPS, is further processed, e.g., separation by 2gel electrophoresis, followed by staining with e.g., silver nitrate. The intensity of stained spots, representing individual regulatory proteins, is compared to their corresponding expression in control tissue.

Because different cells display a unique profile of ubiquitinated and non-ubiquitnated regulatory proteins under different conditions, the distinct profile of the IPS that is presented by specific disease states can be determined and used for improved diagnostic purposes.

Accordingly, in a second aspect, the invention features a diagnostic method for determining the presence of disease or pathology in a biological sample, comprising (a) contacting a test biological sample with a ubiquitin-binding protein, such that IPS proteins bind to the ubiquitin-binding protein; (b) isolating the IPS proteins; (c) analyzing the isolated IPS proteins, wherein an expression profile is generated; and (d) comparing the test expression profile with a control expression profile to determine if the test profile differs from the control profile, wherein differences from the control profile indicate the presence of disease or pathology.

In a third aspect, the invention features a kit for diagnosing the presence of pathology or disease in a biological sample by generating a protein profile for the biological sample and comparing the protein profile generated with the fingerprint of a normal healthy tissue or cell corresponding to the biological sample tested. In this aspect, the invention features a kit comprising an ubiquitin-binding protein or proteins capable of binding the appropriate IPS or subset. In addition, such a kit may optionally comprise one or more of the following: (1) instructions for using the ubiquitin-binding protein for diagnosis, prognosis, therapeutic monitoring or any combination of these applications; (2) a labeled binding partner to the binding protein or proteins; (3) a solid phase (such as a reagent strip) upon which the binding protein(s) is (are) immobilized; and (4) a label or insert indicating regulatory approval for diagnostic, prognostic or therapeutic use or any combination thereof. If no labeled binding partner to the binding protein(s) is (are) provided, the protein itself can be labeled with a detectable marker, e.g., a chemiluminescent, enzymatic, fluorescent, or radioactive moiety.

More generally, the method of the invention provides a database of protein expression profiles, or fingerprints, generated by the protein profiling method of the invention from a variety of normal and abnormal cells and tissues. Each class of tumor, for example, will express a unique 'fingerprint' of proteins, providing a distinct molecular signature for each disease state useful for as a diagnostic tool.

Further, the protein profiling method of the invention allows a further subset of the IPS which reflects proteins with increased or decreased expression in the presence of disease or pathology relative to the corresponding set from a control (normal, non-diseased) sample.

In a fourth aspect, the invention features a database of protein expression fingerprints, each unique for a disease state, comprised of two or more protein profiles generated by the steps of: (a) contacting a biological sample with a ubiquitin-binding protein, such that the Indicator Protein Set (IPS) proteins bind to the ubiquitin-binding protein; (b) isolating the IPS proteins; and (c) analyzing the isolated IPS, wherein an expression profile of an IPS for each the tissue or cell is established.

Establishing a disease specific fingerprint provides a rapid method for diagnosis of that disease comprising detecting in a relevant biological sample the protein profile of the IPS for comparison with the corresponding control sample in order to determine if the disease is present. These methods are also suitable for clinical screening, prognosis, monitoring the results of therapy, identifying patients most likely to respond to a particular therapeutic treatment drug screening and development, and identification of new targets for drug treatment.

In a fifth aspect, the invention features a key subset of an IPS which represent proteins which exhibit an altered level of expression in the presence of an aberrant condition, e.g., disease onset, pathology, transformation, etc. The alteration includes increased and decreased expression, as well as post-translational modifications, such as phosphorylation. The presence of these key indicator proteins are diagnostically useful for indicating the alteration of cells or tissue from a normal healthy condition to an aberrant or pathological condition. Specifically, antibodies can be generated against a subset of the IPS, and these antibodies can be deposited on a protein-chip using available technology. A biological sample can then be applied directly to the protein-chip, and the levels of each protein that is recognized by the particular set of antibodies that is immobilized on the chip, is quantitated to distinguish between normal and aberrant states.

In a sixth aspect, the invention features drug discovery and validation methods by monitoring the effect of a test compound or drug on the expression of the IPS. In one embodiment, the invention features a method of identifying a compound able to modulate the protein profile of an Indicator Protein Set (IFS) of interest, comprising: (a) contacting a biological sample exposed to a test compound with a ubiquitin-binding protein, such that the IPS proteins bind to the ubiquitin-binding protein; (b) isolating the IPS proteins; and (c) analyzing the isolated Indicator Protein Set, wherein the effect of the test compound on the expression profile of the Indicator Protein Set is determined.

Of particular interest is identification of a compound which modulates expression of an IPS from aberrant to normal. Such a compound could further be tested for ability to ameliorate a disease condition or inhibit disease development.

In a seventh aspect, the invention features an Indicator Protein Set (IPS) identified by the method of: (a) contacting a biological sample with a ubiquitin-binding protein, such that the IPS proteins bind to the ubiquitin-binding protein; and (b) isolating the IPS proteins; wherein the isolated ubiquitinated and non-ubiquitinated proteins generate the IPS.

The ubiquitinated proteins become constituents of the IPS following the removal of the ubiquitin moieties. The identity of the IPS (which, includes both ubiquitinated and non-ubiquitinated proteins, is an important aspect of this invention, can be determined by Tandem Mass Spectrometry (MS), as described below.

The Protein Profiling methodology requires the determination of both the pattern of expression of cellular ubiquitinated and non-ubiquitinated proteins, as well as their abundance. Available scanning software can be used for the precise quantitation of protein spots that are detected by 2D gel analysis.

In a related aspect, the invention features an IPS isolated from a cell or tissue sample, which is subject to limited proteolytic digestion, e.g., with trypsin, and then subject to Tandem-mass spectrometric (MS) analysis. This approach allows identification of each member of the IPS and/or the subset of key indicator proteins exhibiting altered expression in the presence of disease or pathology relative to expression in a normal healthy sample. An important advantage of this approach is that much lower amounts of protein is required. Although a large fraction of the signal in the MS analysis would be generated by ubiquitin, the peaks representing proteolytic fragments that are derived from ubiquitin are known and can be ignored. A second advantage of MS analysis is that it is very rapid and is readily adaptable to automation and high throughput applications.

In an eighth aspect, the invention features a protein expression fingerprint specific for a disease or condition, and specific for a cell or tissue, comprising one or more proteins in the IPS that was isolated by the above described method, in which proteins exhibit an altered expression in the disease state relative to a corresponding non-diseased control cell or tissue.

In a ninth aspect, the invention offers a method to determine if a protein of interest is a target of ubiquitination in vivo. Specifically, the method comprises (a) contacting a biological sample containing the protein of interest with a ubiquitin-binding protein, such that ubiquitinated proteins bind to the ubiquitin-binding protein; and (b) determining if the protein of interest is present.

In more specific embodiments, step (b) can be performed using immunological or other detection methods known to the art.

In a tenth aspect, the invention permits the examination of the entire pool of ubiquitinated proteins that are associated with the ubiquitin-binding protein, to survey the levels of well-characterized targets that have been previously associated with disease. Specifically, the method comprises: (a) contacting a biological sample with a ubiquitin-binding protein, such that ubiquitinated proteins bind to the ubiquitin-binding protein; and (b) determining if proteins of interest are present.

In a separate aspect, the invention encompasses a method of using protein-chip for high throughput analysis of the effect of drug screens on the expression profile of the IPS, and a method for using protein-chip technology for high throughput diagnostic analysis of biological samples from peripheral blood, body fluids, tissue biopsy, or stool sample. The biological sample will also include cultured cells and protein extracts from any source, to distinguish between normal and aberrant states. Other objects and advantages will become apparent from a review of the ensuing detailed description taken in conjunction with the following illustrative drawing.

In another separate aspect of the invention, multiple GST-UBA domain matrices may be used simultaneously to increase the number of ubiquitinated and non-ubiquitinated proteins that are isolated. Since each UBA domain has limited substrate specificity, they may be used in combination to isolate a larger number of ubiquitinated and certain non-ubiquitinated proteins.

In a yet further aspect of the invention, an alternate strategy for identifying UBA-interacting proteins is by digesting the entire population of proteins bound to UBA-containing matrices with trypsin, resolving the peptides by high performance liquid chromatography, and performing a final analysis by mass-spectrometry. The peptide peaks that correspond to sequences derived from ubiquitin are ignored, and only those that originate from other cellular proteins are characterized. This alternate strategy eliminates the need for the de-ubiquitination step and subsequent 2D gel electrophoresis and permits adaptation of the technique to robotics and automation for high throughput screening.

DETAILED DESCRIPTION OF THE INVENTION

Figure 1:
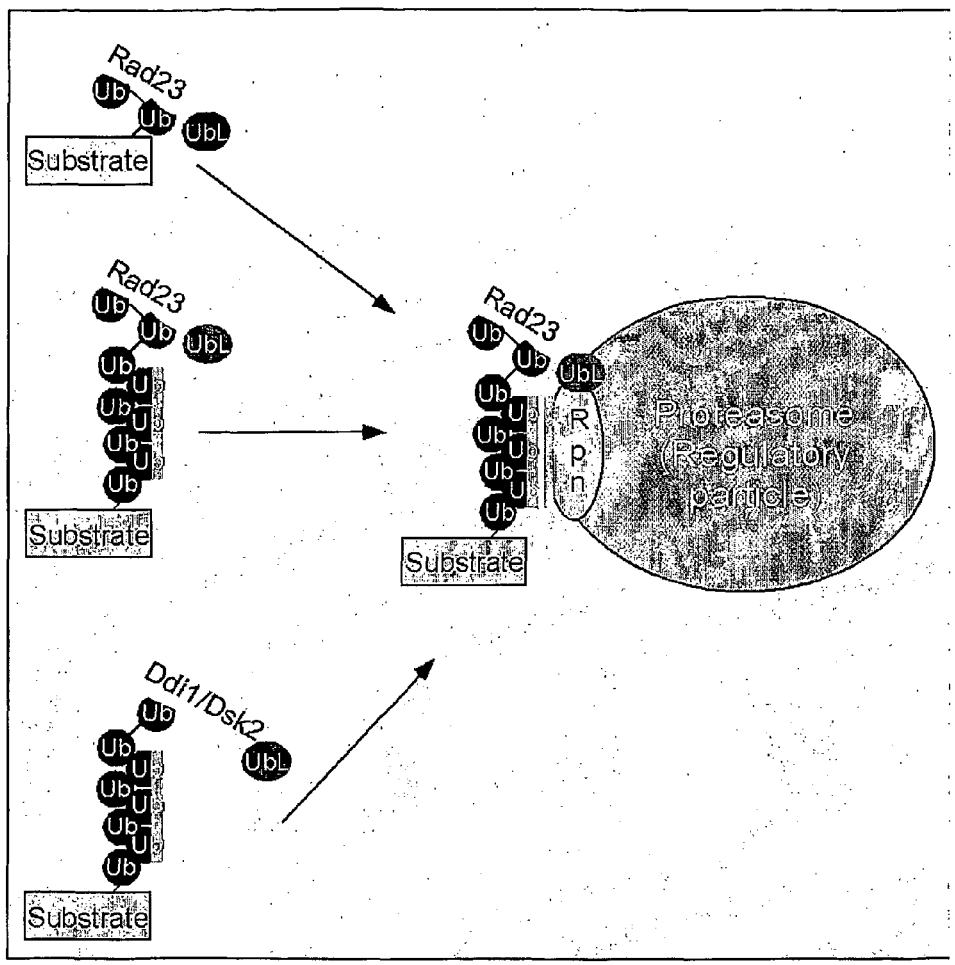
FIG. 1. A model of Rad23 binding to the proteasome through its UbL domain, and with multi-Ub chains through UBA sequences.

Before the present methods are described, it is to be understood that this invention is not limited to particular assay methods, test compounds and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a complex" includes mixtures of such complexes, reference to "the compound" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

The term "protein profiling" means a method of quantitating the expression of a specific set of key proteins involved in cellular regulation and growth, comprising the population of ubiquitinated and non ubiquitinated proteins isolated in the method of the invention by binding to a ubiquitin-binding protein, e.g., Rad23.

By the term "Indicator Protein Set" or "IPS" is meant a subset of cellular proteins identified by binding to ubiquitin-binding protein, which display a cell or disease specific distinct protein expression pattern. In certain instances, if only one component of a multisubunit complex is ubiquitinated, its interaction with the UBA matrix would yield a single ubiquitinated protein, as well as additional non-ubiquitinated factors, which may include certain non-ubiquitinated proteins that are present in the complex. However, all of the proteins could have potential diagnostic value and are therefore included in the "Indicator Protein Set". By the term "subset" of an IPS, or "key subset" is meant one or more of the ubiquitinated proteins comprising the IPS which are established to exhibit an altered expression in an aberrant or disease or pathological condition relative to the corresponding expression found in a normal healthy sample. The key subset proteins may include proteins that show an increased or decreased expression in the presence of disease relative to the appropriate control, or exhibit a structural or functional change relative to the control protein, including a change in phosphorylation or glycosylation.

"Protein expression fingerprint" is the expression pattern of an Indicator Protein Set isolated and analyzed by the method of the instant invention.

By the term "a database of protein expression fingerprints", or "a database of protein profiles" is meant a collection of two or more protein expression fingerprints characterizing specific cell or tissues in both normal and aberrant conditions.

By the term "modulate" is meant, in one context, the ability of a compound to alter the protein expression fingerprint of a cell or tissue. Preferably, a drug candidate will be identified by its ability to alter the fingerprint of a cell towards the profile of the corresponding normal, non-disease cell. Based on the present disclosure, such modulation can be determined by assays known to those of skill in the art or described herein.

The term "change" includes "increase" and "decrease" and refers to the relative increase or decrease in abundance of an Indicator Protein or the relative increase or decrease in expression or activity of an Indicator Protein in a first sample or sample set compared to a second sample (or sample set). A change may be measured by any technique known to those of skill in the art, albeit the observed increase or decrease will vary depending upon the technique used. Preferably, change is determined herein as described in the Examples infra, and includes, for example, differences in silver nitrate staining intensity.

By the term "aberrant" condition is meant a condition which is different from that of the normal, healthy, disease-free state. Aberrant includes conditions of disease onset, disease development, transformation, etc. The term also encompasses environmental stresses, including but not limited to mechanical stress and temperature, as well as the effect of drugs and other pharmaceuticals, that could manifest a difference in protein expression patterns in otherwise normal cells.

General Aspects of the Invention

Ubiquitin (Ub) is a 76 amino acid protein that is highly conserved in eukaryotes, and is covalently linked to other proteins to mark them for degradation by a protease called the proteasome. The human Rad23 protein binds ubiquitinated proteins in vivo. The binding interaction is sufficiently strong to withstand high salt and denaturing conditions. This feature was studied to develop a method for selectively purifying ubiquitinated proteins, which represent the most important known regulators of cell growth and development. Because of their physiological role, the expression of ubiquitinated proteins can be used diagnostically to determine the presence of malignancy or the development of a disease condition by comparing the protein profile fingerprints of ubiquitinated proteins in a healthy cell relative to that of a diseased cell. Virtually all the important regulators of cell growth and development are targeted for degradation by the ubiquitin pathway. Transformation of cells by viruses, or their altered growth properties in cancer require that the pattern of growth control be altered. Examples of proteins that are degraded by the ubiquitin pathway include, but are not limited to, tumor suppressors (p53 and Rb), inhibitors of the inflammatory response (IBα), signal tranduction molecules (c-Jun, c-Myc, and G-alpha), cell cycle regulators (cyclins, CDK inhibitors, cohesions and Pds1), topoisomerases.

Current methods for monitoring global gene expression primarily rely on gene-chip/DNA microarray technology. This approach has several disadvantages, including high costs, long duration times for conducting the assay, and inability to selectively examine only those genes expected to have predictive functionality. Furthermore, the correlation between mRNA expression and requirement of the protein product under specific environmental conditions has been recently shown to be very poor. Consequently, the vast majority of genes detected by, for example, DNA microarray technology, are not beneficial toward identifying and characterizing differences in cell states.

Protein profiling has previously been approached by examining the protein expression of aberrant cells and comparing them to normal cells. In this approach, a small quantity of total protein is isolated from tissues of interest, and analyzed by 2-dimensional gel electrophoresis. Computer programs have been developed to characterize the complex cellular expression profiles. However, a severe limitation of this approach is that the expression of most proteins in the cell is unaffected by transformation, or oncogenesis. This is because most proteins in the cell are stable, abundant and perform structural roles that are required for both normal and aberrant cells. Further, because this approach does not selectively examine key proteins, such as those proteins regulating cell growth, the preponderance of data reflects the expression of uninformative proteins. The high level of stable proteins hinders the detection of important cellular regulators which are short lived, expressed at low levels, and whose stability is controlled by ubiquitin-mediated degradation. This subset of proteins represents critical regulators that are involved in controlling diverse physiological events including cell-cycle progression, stress-response, and signal transduction. The protein profiling method of the invention, however, permits selective purification of ubiquitinated and specific non-ubiquitinated proteins, which represent a set of important cellular proteins. To illustrate the difficulty of monitoring differences in total protein extracts, the stability of proteins over a 30-minute duration was examined. Very few proteins whose levels decreased following the 30 min incubation were detected (results not shown), suggesting that the highly abundant, and stable proteins obscured the detection of short-lived regulators. Thus, it is clear that using total cellular protein is an insensitive way for examining the protein profile of cells.

The method of the instant invention represents a new approach for distinguishing aberrant cells from normal cells, for example, the method of the invention provides a diagnostic tool for the identification of cancer and other cell abnormalities. This method utilizes the changes in protein expression of specific key proteins that occurs in the presence of disease or pathology, relative to the protein expression of the specific proteins in a normal (absence of pathology or disease) cell.

The instant invention represents an advance relative to current approaches because it results in the selective identification and isolation of those proteins that play critical roles in cell growth and development. By eliminating the bulk of cellular proteins, which are primarily noninformative, the expression profile of a small subset of key indicator proteins (IPS) can be determined. The expression profile of the IPS can be used diagnostically to determine the presence of cellular abnormalities. Further, a subset of the IPS, comprised of key indicator proteins may be further selected from the IPS, representing proteins which show an altered expression in the presence of disease or pathology relative to a corresponding normal control sample.

Furthermore, the sensitivity of the protein profiling method can be enhanced through the use of multiple GST-UBA domain matrices. In this manner, the simultaneous use of multiple GST-UBA domains can increase the number of ubiquitinated and non-ubiquitinated proteins that are isolated. This is possible since each UBA domain has limited substrate specificity. Thus, when used in combination, a much larger and diverse group of ubiquitinated (and certain non-ubiquitinated) proteins can be identified.

The protein profiling method of the invention is useful for screening compounds for ability to modulate (e.g., up or down regulate) the profile of the IPS or subset, as well as for validating the therapeutic efficacy of drugs. For example, a drug is expected to reverse or alleviate the detrimental effects of a particular disease. If a drug achieves this effect, protein profiling will confirm that the protein profile of the treated cells regain or return to the expression pattern in normal cells.

In another aspect of the invention, the purified ubiquitinated proteins or IPS isolated for each cell or tissue sample is subjected to limited proteolytic digestion, e.g., trypsin, and then subject to tandem-mass spectrometric (MS) analysis. This allows the identity of each member of each IPS to be established. In contrast to the 2D gel analysis, which only provides a 'finger-print' without any information on the identity of the protein spots, MS offers the potential for direct identification of the important regulators of growth and development, whose levels are affected in disease states. An important advantage of this approach is that much lower amounts of protein is required. Although a large fraction of the signal in the MS analysis would be generated by ubiquitin, the peaks representing proteolytic fragments that are derived from ubiquitin are known and can be ignored. A second advantage of MS analysis is that it is very rapid and is readily adaptable to automation and high throughput applications.

In a yet further aspect of the invention, streamlining of the Protein Profiling Method can be accomplished by elimination of the de-ubiquitination step. In this method, the entire population of proteins bound to UBA-containing matrices is digested with trypsin, the peptides are resolved by high performance liquid chromatography and the peaks are analyzed by mass spectrometry. Those peptide peaks that correspond to sequences derived from ubiquitin are ignored, whereas those that originate from other cellular proteins are characterized. Thus, the need for 2 dimensional gel electrophoresis is eliminated, thus permitting adaptation of the technique to robotics and automation for high-throughput screening.

As shown in the experimental section below, the purification of ubiquitinated and certain non-ubiquitinated proteins with a ubiquitin-binding protein, such as Rad23, involves a single step, which is rapid and quantitatively efficient. The affinity of binding is very high. Rad23 can be purified in large amounts and readily coupled to an affinity matrix. The cost of these materials, e.g., Rad23 protein and affinity matrix, are minimal. Several commercial binding reagents are available, and can be used for immobilizing and stabilizing Rad23.

Further, the time required for isolating the IPS proteins of interest is minimal. Cells can be lysed in 20 seconds, and protein extracts incubated with affinity matrix for 15 minutes. The affinity matrix is then washed in buffer and the bound proteins contain the population of regulators of interest. The entire process can be accomplished in less than 1 hour. The step of analyzing the isolated proteins may be conducted using a number of methods known to those of skill in the art, including direct proteolytic digestion and analysis by mass spectrometry, or analysis by 2D gel electrophoresis. Generally, 2D gel electrophoresis is expected to take about 24 hours, and further staining with silver nitrate may require about 2 hours. Thus, quantitative results can be obtained within 48 hours.

FIG. 1 shows a model for Rad23 binding to the proteasome. Rad23 can interact with substrates that are ligated to multi-Ub chains (black filled circles). The interaction with ubiquitinated substrates transiently inhibits further multi-Ub chain assembly. Rad23 delivers the ubiquitinated substrate to specific multi-Ub chain binding factors in the proteasome, such as Rpn10 (RPN in the figure). The substrate-linked multi-Ub chain appears to mediate an interaction between Rad23 and Rpn10, since each protein recognizes a different feature in the chain. The interaction between Rpn10 and the multi-Ub chain is mediated by hydrophobic interactions, which is indicated by the shaded stripe alongside the multi-Ub chain and Rpn10. In contrast, Rad23 may interact with the distal Ub moieties in a multi-Ub chain. It is suggested that proteasome-associated E2 and E3 factors could further ubiquitinate the substrate to promote efficient degradation. This scheme also anticipates that other UBA and UbL containing proteins, including Ddi1 and Dsk2, perform similar roles in the delivery of proteolytic substrates and regulators to the proteasome.

Analytical Methodology

As used herein, "two-dimensional electrophoresis" (2D-electrophoresis) means a technique comprising isoelectric focusing, followed by denaturing electrophoresis; this generates a two-dimensional gel (2D-gel) containing a plurality of separated proteins. Preferably, the step of denaturing electrophoresis uses polyacrylamnide electrophoresis in the presence of sodium dodecyl sulfate (SDS-PAGE). Highly accurate and automatable methods and apparatus for conducting 2D-gel electrophoresis are known to the art, and described in publications such as WO 98/23950, and U.S. Pat. No. 6,064,754, each of which is incorporated herein by reference in its entirety. Briefly, 2D-gel electrophoresis provides efficient, computer-assisted methods and apparatus for identifying, selecting and characterizing proteins in a biological sample. A two-dimensional array is generated by separating biomolecules on a two-dimensional gel according to their electrophoretic mobility and isoelectric point. A computer-generated digital profile of the array is generated, representing the identity, apparent molecular weight, isoelectric point, and relative abundance of a plurality of biomolecules detected in the two-dimensional array, thereby permitting computer-mediated comparison of profiles from multiple biological samples, as well as computer aided excision of separated proteins of interest.

The protein expression profile fingerprints of the invention are established qualitatively or quantitatively by any method known to those skilled in the art, including but not limited to the methodology described herein, kinase assays, enzyme assays, binding assays and other functional assays, immunoassays, and western blotting. In one embodiment, the fingerprints are established by quantitative detection by analysis on a 2D gel by virtue of their MWs and pIs and visualized by staining the gel. In one embodiment, proteins separated by gel electrophoresis are visualized and quantified by silver nitrate or copper iodide staining. Methods for visualizing separated proteins are known to the art and are described. See, for example, Root et al. (1993) Anal. Biochem. 209:354-359; Gottlieb et al. (1987) Anal. Biochem. 165:33-37; Syrovy et al. (1991) J. Chromatog. 569:175-196; Draber (1991) Electrophoresis 12:453-456; Patton et al. (1994) Anal. Biochem. 220:324-335; Root et al. (1990) Anal. Biochem 186:69-73. In another embodiment, the IPS or subset of key indicator proteins are stained with a fluorescent dye and imaged with a fluorescence scanner. Sypro Red (Molecular Probes, Inc., Eugene, Oreg.) is a suitable dye for this purpose. Another fluorescent dye is Pyridinium, 4-[2-[4-(dipentylamino)-2-trifluoromethylphenyl]ethenyl]-1-(sulfobutyl)-, inner salt.

Alternatively, the expression profile of the relevant Indicator Protein set or subset can be established by detection in an immunoassay. In one embodiment, an immunoassay is performed by contacting a biological sample from a subject to be tested with an relevant antibodies under conditions such that immunospecific binding can occur if a protein from the IPS or subset is present, and detecting or measuring the amount of any immunospecific binding by the antibody. Antibodies can be produced by the methods and techniques known to the art, as well as those discussed below.

In addition to the use of antibodies for quantitative detection of an IPS or subset to establish an expression profile, any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

Antibody Methodology

According to the invention an IPS or subset protein may be used as an immunogen to generate antibodies which immunospecifically bind such an immunogen. Such immunogens can be isolated by any convenient means, including the methods described above. Antibodies of the invention include, but are not limited to polyclonal, monoclonal, bispecific, humanized or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein refers to immunoglobulin molecules and immunologically active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

In one embodiment, antibodies that recognize an IPS or subset protein may be commercially available. In another embodiment, an antibody to an IPS or subset protein may be generated by known methods of antibody production. In a specific embodiment, hydrophilic fragments of an IPS or subset protein are used as immunogens for antibody production. In the production of antibodies, screening for the desired antibody can be accomplished by techniques known in the art, e.g. ELISA (enzyme-linked immunosorbent assay). Polyclonal antibodies which may be used in the methods of the invention are heterogeneous populations of antibody molecules derived from the sera of immunized animals. Unfractionated immune serum can also be used. Various adjuvants may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or corynebacterium parvum. Additional adjuvants are also well known in the art.

For preparation of monoclonal antibodies (mAbs) directed toward an IPS or subset protein, any technique providing for the production of antibody molecules by continuous cell lines in culture may be used. For example, the hybridoma technique originally developed by Kohier and Milstein (1975) Nature 256:495-497), as well as the trioma technique, the human B-cell hybridoma technique (Kozbor et al. (1983) Immunology Today 4:72), and the EBV-hybridoma technique to produce human monoclonal antibodies (Cole et al. (1985) in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mabs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g., human-mouse chimeras). A chimeric antibody is a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.)

Chimeric and humanized monoclonal antibodies can be produced by recombinant DNA techniques known in the art, for example, using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443.

Ubiquitin-Binding Proteins

The method of the invention provides a ubiquitin-binding protein, such as Rad23, Ddi1, Dsk2 and Rpn10. However, the use of other proteins with similar properties is considered a part of this invention. Ubiquitin-binding proteins may be obtained from any species from which the genes are available. The proteins may be expressed as fusions to glutathione-SEPHAROSE®, thioredoxin, maltose-binding protein, His-6 epitope, Flag-epitope, or any one of many other well-characterized epitopes to which affinity reagents or antibodies are available. The ubiquitin-binding proteins could also be cross-linked to specific antibodies that are coupled to a matrix. The preparation of matrices, linked to various derivatives of ubiquitin-binding proteins described above, are considered a part of this invention. In addition, any of the above mentioned ubiquitin-binding proteins (lacking the aforementioned epitopes and tags), could be directly coupled to cyanogen-activated SEPHAROSE®, and used as an affinity matrix. Further, proteins that participate in the enzymology of protein ubiquitination form transient interactions with ubiquitin, and may also prove useful in binding ubiquitinated proteins.

Furthermore, the UBA domain from any species can be constructed de novo by peptide synthesis, and cross-linked to a solid support medium. In addition, the sequence of the synthetic UBA peptide (~30 amino acid residues) can be altered to generate domains that have specific enhanced features that can be detected by interaction with target proteins. This same technique can be used to assemble multimeric and hybrid forms of UBA affinity matrices.

In addition to the intact ubiquitin-binding proteins, affinity reagents that contain only the UBA sequences from Rad23, Ddi1, Dsk2, ataxin-3 and p62 may be generated for use in the method of the invention. Similarly, the ubiquitin-binding motif in proteins such as Rpn10/S5a may also be used for the generation of an affinity matrix useful in the method of the invention. The UBA domain forms a specific interaction with Ub, and is sufficient for high-affinity interaction with ubiquitinated cellular proteins. Some of these domains also interact with specific non-ubiquitinated proteins. Affinity reagents that contain multiple, tandemly linked UBA domains will also be examined, as they may confer higher binding efficiency against ubiquitinated and non-ubiquitinated proteins. The proteins will be expressed and purified from E. coli, which lacks the ubiquitin/proteasome system. The construction of these chimeras, their method of purification, and the preparation of affinity reagents are considered a component of this technology. It should be noted that the generation of synthetic peptides, and other synthetic molecules, for the recognition of ubiquitin-binding molecules (including haptens and allosteric effectors of antibody/antigen interactions), are considered a part of this technology.

The various UBA containing proteins (Rad23, Dsk2, Ddi1, ataxin-3 and p62) perform overlapping, but non-redundant functions. It is predicted therefore that they will interact with an overlapping, but not entirely redundant spectrum of cellular ubiquitinated and non-ubiquitinated proteins. For instance, Rad23 binds between ~25% of total cellular ubiquitinated proteins in actively growing cells. However, the family of UBA-containing proteins may collectively bind a much larger fraction of cellular ubiquitinated proteins. This result offers a distinct advantage in the implementation of the technology because it provides a means for selectively purifying different cohorts of important regulators of cell growth and development, based on which UBA-containing protein is used.

Figure 2:
FIG. 2. Fusion proteins encoding GST-UBA from yeast and both human Rad23 proteins were expressed and purified to near homogeneity from *E. coli*. All the constructs were examined for interaction with ubiquitinated proteins in cell extracts, and were found to be largely equivalent.
Figure 3:
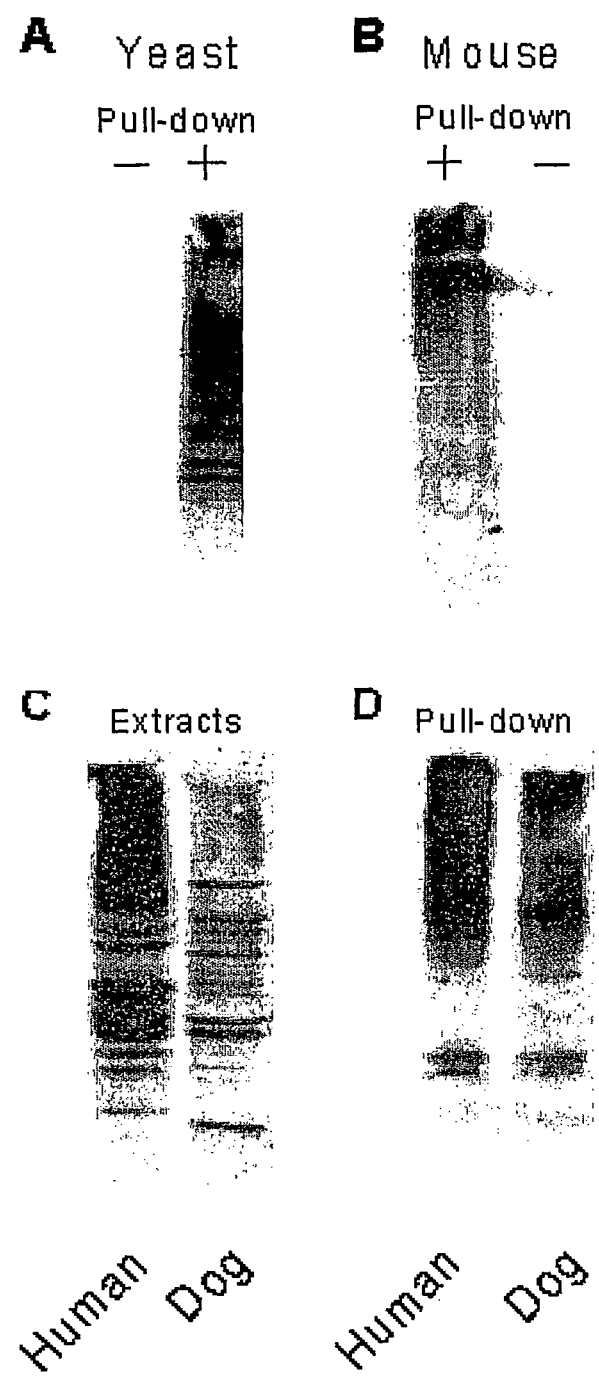
FIG. 3. GST-UBA1 from yeast Rad23 was crosslinked to a SEPHAROSE® matrix (polyUb affinity beads), and incubated with equal amounts of protein extracts prepared from yeast, mouse, dog and human cells. Protein extracts that were applied to polyUBA1 interacted with ubiquitinated proteins across species. The protein extracts were examined by immunoblotting, using anti-ubiquitin antibodies. Panel A: Protein extracts from yeast Saccharomyces cerevisiae were applied to mock (−) or polyUb affinity beads (+). Panel B: Protein extracts from mouse were applied to mock (−) and polyUb affinity beads(+). Panel C: Total cellular extracts from human cultured cells and dog tissue were examined. Panel D: Samples as in Panel C were applied to polyUb affinity beads. All four filters were probed with anti-ubiquitin antibodies and developed by enhanced chemiluminescence.

It has been established that the UBA domain is a universal ubiquitin (Ub)-binding domain, since sequences derived from different proteins can each bind Ub. The two UBA domains from yeast Rad23, as well as the two UBA domains present in both human hR23A and human hR23B can each bind ubiquitinated cellular proteins with high affinity. All six GST-UBA sequences have been purified to homogeneity as shown in FIG. 2. When GST-UBA1, prepared from yeast Rad23 protein, was applied to protein abstracts prepared from yeast, mouse, dog and human cells, a high affinity interaction with ubiquitinated proteins was observed in all cases (FIG. 3).

Figure 4:
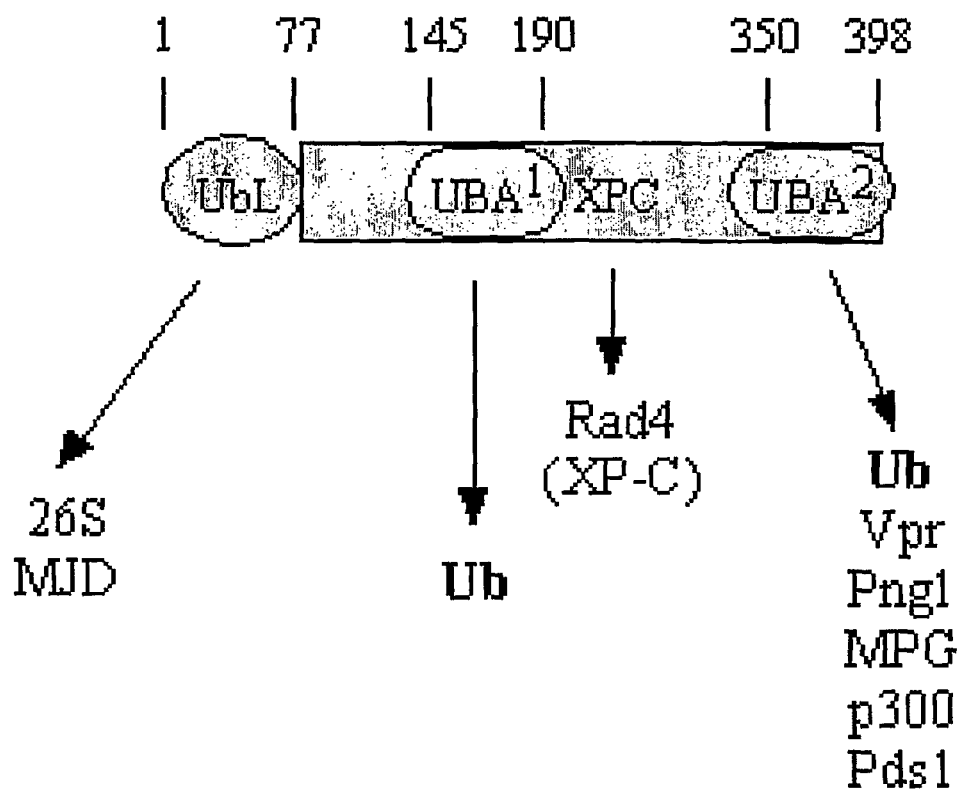
FIG. 4. The general domain structure of Rad23 proteins is shown. Rad23 proteins have been isolated from yeast, plants, mouse and humans, and they are all similar. The amino-terminal ubiquitin-like (UbL) domain can interact with catalytically active 26S proteasome, as well as ataxin-3, the causative agent in the human neurodegenerative condition Machado-Joseph Disease (MJD). In addition, Rad23 proteins contain two UBA sequences that are structurally indistinguishable. Although both UBA1 and UBA2 can bind ubiquitin, and multiubiquitin chains, only UBA2 binds other proteins that are not ubiquitinated. Among this set of proteins is the HIV-1 encoded protein, Vpr; a protein deglycosylating enzyme, Png1; a methyladenine deglycosylase DNA repair protein, MPG; and the transcription adaptor molecule, p300. It is likely that UBA2 also interacts with Pds1, a regulator of DNA damage induced checkpoints, and the G1->M phase cell-cycle transition.

Rad23 proteins contain two UBA domains (UBA1 and UBA2) that are structurally indistinguishable. Although both UBA domains can bind Ub, they have specificity towards certain non-ubiquitinated regulatory proteins (FIG. 4). Because these characteristics can differ subtly from the binding properties of the individual UBA domains, it is likely that the 3-dimensional arrangement of the two UBA domains within the intact Rad23 protein contributes to additional specificity.

Figure 5:
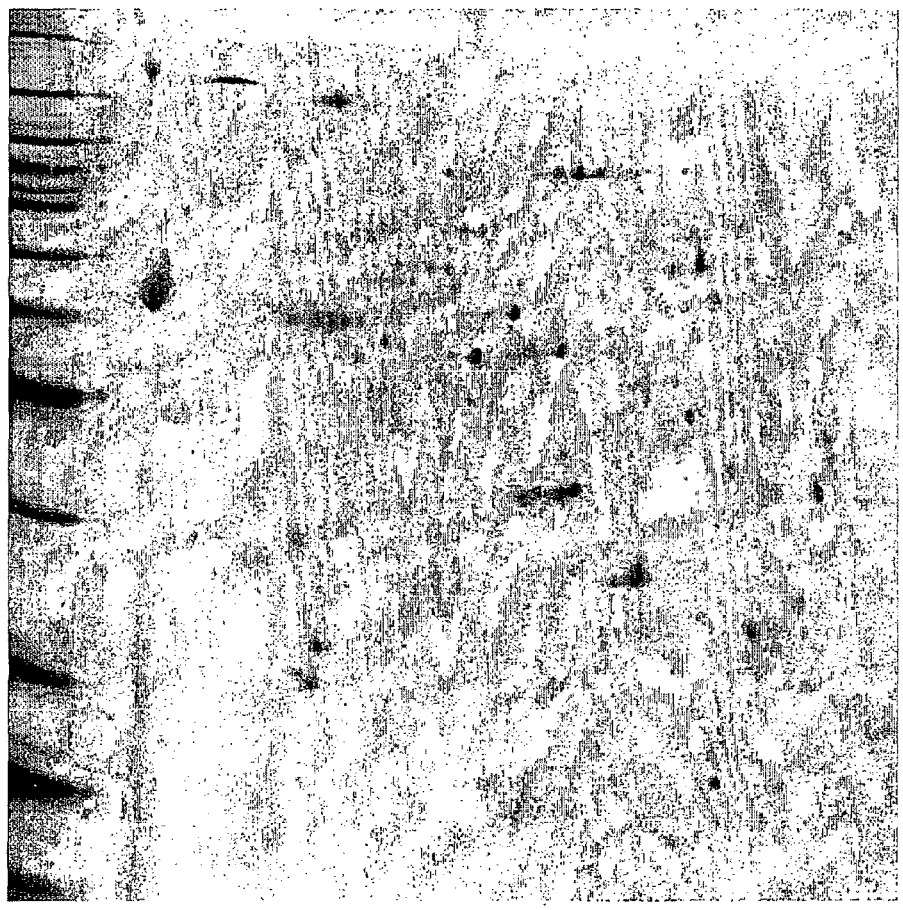
FIG. 5. Rad23 protein was purified and the associated factors were separated by 2D gel analysis, and visualized by silver staining. Approximately 100 protein spots can be detected.

With the use of specific UBA-affinity reagents, different sets of regulatory and ubiquitinated proteins can be isolated. This is an important constraint, since the intact Rad23 protein binds greater than 100 cellular proteins in the absence of stress-inducing conditions, as shown in FIG. 5, and it would be useful to refine the set of interacting factors by using distinct UBA domains.

Certain UBA domains can bind both ubiquitinated and non-ubiquitinated regulatory proteins, as shown in FIG. 4. Specific reagents have been generated that permit identification of both classes of proteins.

Diagnostic Methodologies

In accordance with the present invention, test biological samples of cerebrospinal fluid (CSF), serum, plasma or urine obtained from a subject suspected of having or known to have disease or pathology can be used for diagnosis or monitoring. In one embodiment, a protein expression profile for an IPS or subset typical of the presence of an aberrant condition in a test biological sample relative to a control sample (from a known healthy control sample/subject) or a previously determined control reference range protein profile for the corresponding IPS or subset indicates the presence of the aberrant condition. In another embodiment, where one or more key indicator proteins have been identified as indicative of an aberrant condition, the increased or decreased expression of one or more key indicator proteins relative to the corresponding control indicates the presence of the aberrant condition. Additionally, the modification of one or more key indicator proteins in the IPS (including, but not limited to phosphorylation, acetylation, methylation, ADP-ribosylation, nitrosylation, fatty-acid and carbohydrate addition, proteolytic processing or conjugation to ubiquitin-like modifiers), indicates a difference from the normal range and predicts an aberrant condition.

Figure 6:
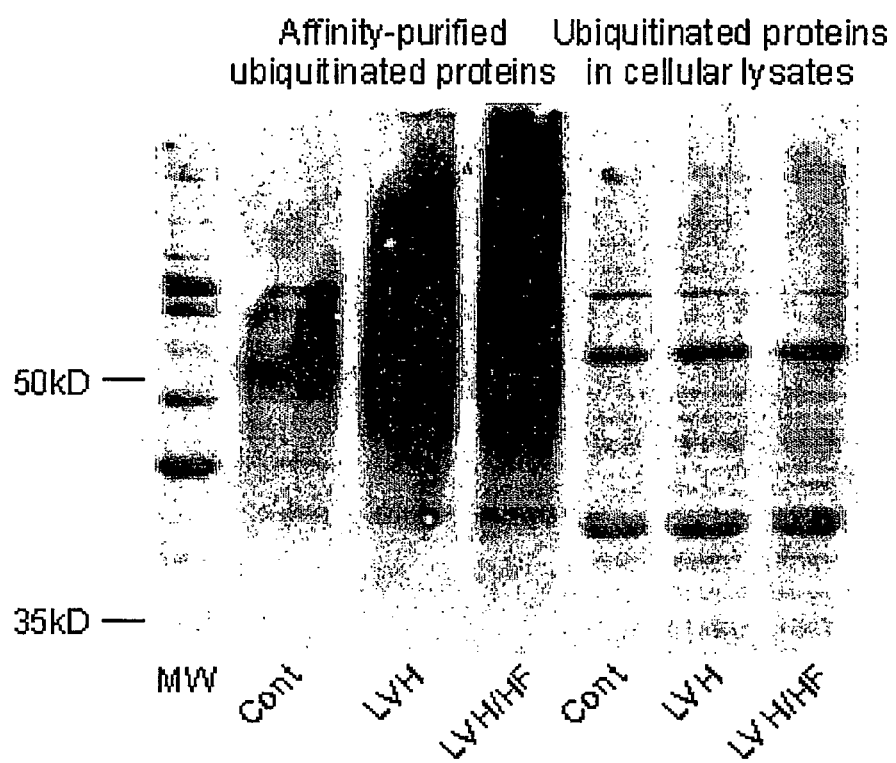
FIG. 6. Protein extracts were prepared from control dog cardiac tissue (cont), and from dogs suffering from left ventricular hypertension (LVH), and animals that had succumbed to heart failure (LVH/HF). The set of lanes on the left of a one-dimension SDS-polyacrylamide gel shows that significantly more ubiquitinated proteins bind GST-UBA in LVH and LVH/HF extracts, in comparison to cont. extracts. The immunoblot was reacted with antibodies against ubiquitin, and detected by enhanced chemiluminescence. The right set of three lanes shows that the overall level of ubiquitinated proteins increases slightly in LVH and LVH/HF cells.
Figure 7:
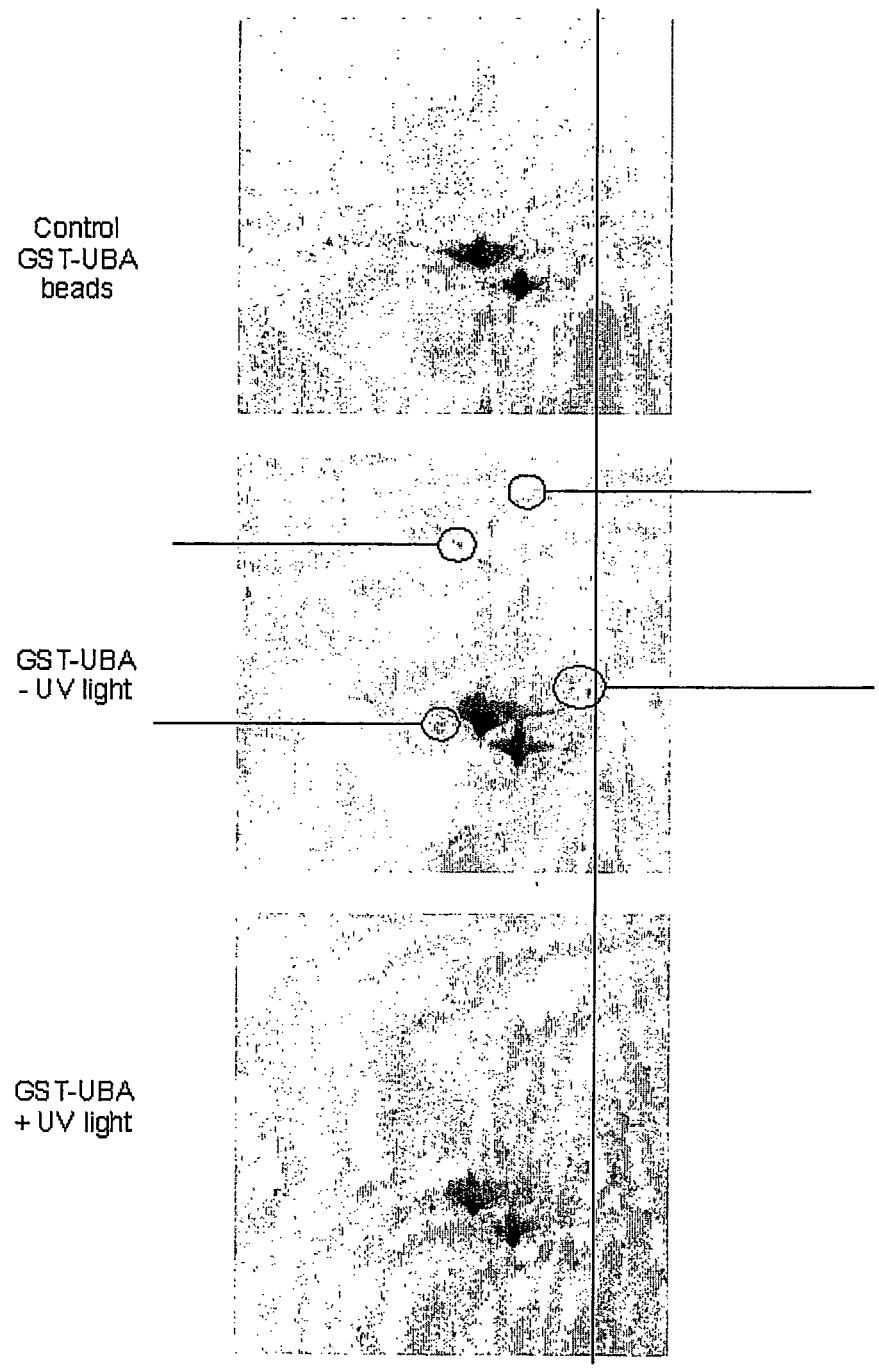
FIG. 7. Human breast cancer cells were exposed to DNA damage (UV light) and the protein extracts incubated with GST-UBA. The upper panel shows the background proteins present on the affinity matrix alone. Note that the highly abundant spots in the middle of the gel represent the GST-UBA protein and a prominent breakdown product containing primarily GST. However, following incubation with breast cancer cell extracts, distinct proteins are detected on the GST-UBA column (indicated by circles and a line). Intriguingly, treatment with UV-light resulted in a marked reduction in the levels of some of these factors, demonstrating that stress conditions can alter the protein expression profile in vivo.

To date, the Protein Profiling technique has been successfully tested in yeast, mouse, dog and human cells, and specific factors were isolated in sufficient quantity to identify them by mass spectrometry. Specifically, tissue-specific and stress-induced differences in protein expression patterns in human cells were detected with the UBA affinity reagents. Moreover, in a canine cardiac model system, different proteins were detected in control animals, and in protein extracts derived from heart tissue from animals having persistent left-ventricular hypertension (LVH) and animals undergoing cardiac failure (HF). This study established unequivocally that different amounts of ubiquitinated proteins could be isolated in association with GST-UBA during these different cell states (FIG. 6), validating the Protein Profiling hypothesis. Similar results were observed in human breast cancer cells that were exposed to ultraviolet-light induced DNA damage (FIG. 7), confirming that differences in protein expression following stress can be detected.

Figure 8:
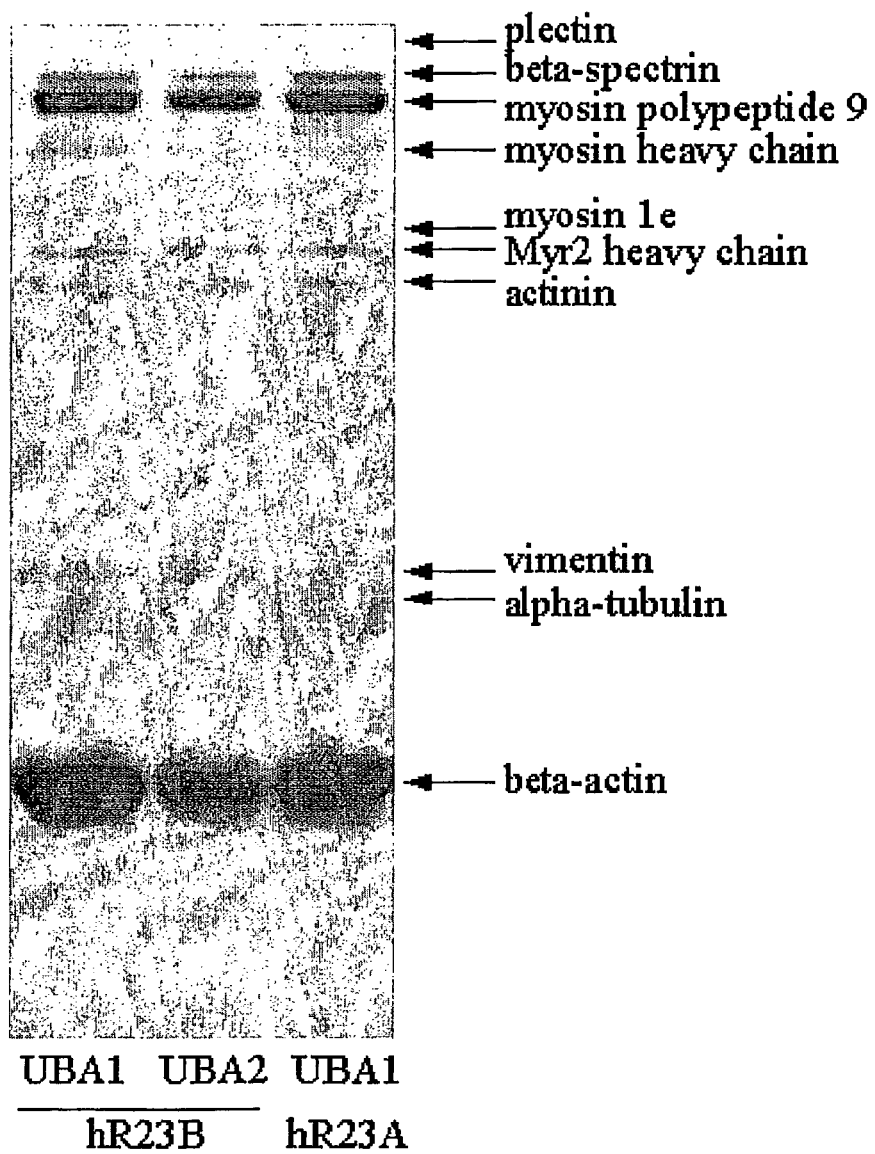
FIG. 8. In a variation of the technique, breast cancer cell extracts were incubated with GST-UBA and a large set of cytoskeletal proteins were identified by mass spectrometry. The identity of each major band is indicated on the right of the figure. Note that in the original gel many additional proteins were visible, although they have not been subjected to further analysis. We believe it is significant that all the proteins identified thus far are components of the cytoskeleton, and this could provide a unique opportunity to monitor cell differentiation and transformation.

It is envisioned that the UBA reagents identified in the instant application represent a powerful new tool for monitoring differences in cell growth. To illustrate this point, human cell proteins were isolated on the UBA affinity reagents and purified in sufficient quantity for identification by mass spectrometry. GST-UBA affinity reagents derived from Human Rad23 proteins bound with very high affinity to a large set of cytoskeletal proteins in human breast cancer cells (FIG. 8). In contrast, abundant housekeeping proteins, including alcohol dehydrogenase and pyruvate dehydrogenase were not detected, demonstrating that the interaction between cytoskeletal proteins and GST-UBA was specific. All of the isolated factors are well-characterized components of the cytoskeleton, and are required for both cell structure and cell adhesion. It is well established that the rapid proliferation of malignant cells and their accompanying loss of cell adhesion is directly linked to the cytoskeleton. Thus, the GST-UBA reagent provides a tool for monitoring changes in cell growth by monitoring the expression profile of cytoskeletal components. Therefore, this system may prove to be useful as an early indicator of the propensity of cells towards unscheduled cell proliferation.

Figure 9:
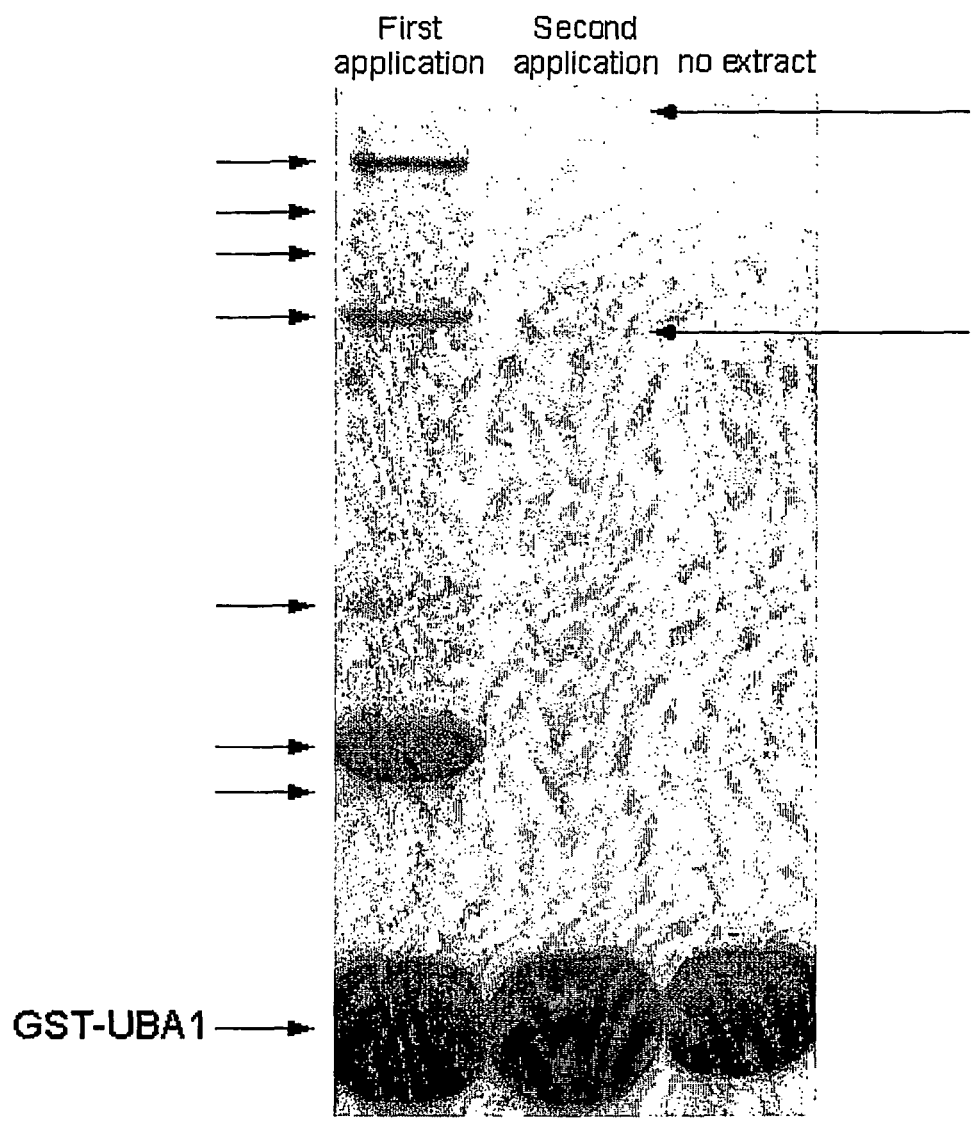
FIG. 9. As in FIG. 7, GST-UBA can be used to isolate a large set of proteins from breast cancer cells (First application). However, when the supernatant from the first application was reapplied to new GST-UBA affinity matrix, we observed that all the highly abundant factors had been removed. However, the lower abundance factors, as well a few new species (indicated by the arrows) were detected. This result indicates that there is competition between the highly abundant factors and the lower abundance proteins for interaction with the UBA domains. A mock reaction is shown in the right lane.

Moreover, it is an object of the present invention to fine-tune the methodology such that ubiquitin binding proteins with lower binding affinity can be readily identified. This may be accomplished by pre-clearing cellular protein extracts with various GST-UBA matrices. Thus, the more abundant factors that bind GST-UBA, or those that have higher binding affinity, can be initially bound and removed on GST-UBA1. The post-adsorbed supernatant, which presumably contains proteins that are linked to short ubiquitin chains (weaker affinity), as well as non-ubiquitinated regulatory proteins that can bind UBA, might then be isolated. This is shown in FIG. 9, wherein the abundant factors, when removed, allowed for the detection of the low abundance proteins. Thus, in accordance with the present invention, a pre-clearing step may be necessary to permit isolation of the less abundant or lower affinity proteins, which may also be significant in terms of their diagnostic value.

Screening Methodologies

The invention provides methods for identifying agents (e.g., candidate compounds or test compounds) that can alter the protein expression pattern of an IPS or subset such that the aberrant expression pattern is ameliorated, e.g., bears closer resemblance to the healthy fingerprint. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. Nos. 5,738,996; and 5,807,683, each of which is incorporated herein in its entirety by reference).

In another separate aspect of the invention, multiple GST-UBA domain matrices may be used simultaneously to increase the number of ubiquitinated proteins that are isolated. Since each UBA domain has limited substrate specificity, they may be used in combination to isolate a larger number of ubiquitinated and certain non-ubiquitinated proteins.

In a yet further aspect of the invention, an alternate strategy for identifying UBA-interacting proteins is by digesting the entire population of proteins bound to UBA-containing matrices with trypsin, resolving the peptides by high performance liquid chromatography, and performing a final analysis by mass-spectrometry. The peptide peaks that correspond to sequences derived from ubiquitin are ignored, and only those that originate from other cellular proteins are characterized. This alternate strategy eliminates the need for the de-ubiquitination step and subsequent 2D gel electrophoresis and permits adaptation of the technique to robotics and automation for high-throughput screening.

In one embodiment, agents that alter the expression of an IPS protein through direct interaction are identified in a cell-based assay system. In another embodiment, agents that alter the expression of an IPS protein through direct interaction are identified in a cell-free assay system. In accordance with this embodiment, a native or recombinant IPS is contacted with a candidate compound or a control compound and the ability of the candidate compound to directly bind the IPS protein is determined. If desired, this assay may be used to screen a plurality (e.g. a library) of candidate compounds. Preferably, the IPS protein(s) is first immobilized, by, for example, contacting the IPS protein(s) with an immobilized antibody which specifically recognizes and binds it, or by contacting a purified preparation of the IPS protein(s) with a surface designed to bind proteins. The IPS protein(s) may be partially or completely purified (e.g., partially or completely free of other polypeptides) or part of a cell lysate. Further, the IPS protein(s) subset may be a fusion protein comprising the IPS or subset, or a biologically active portion thereof, and a domain such as glutathionine-S-transferase. Alternatively, the IPS protein(s) can be biotinylated using techniques well known to those of skill in the art (e.g., biotinylation kit, Pierce Chemicals; Rockford, Ill.). The ability of the candidate compound to directly interact with an IPS protein can be can be determined by methods known to those of skill in the art.

In another embodiment, a cell-based assay system is used to identify agents that modulate the expression of a protein, such as an enzyme, or a biologically active portion thereof, which is responsible for the production or degradation of an IPS protein or is responsible for the post-translational modification of an IPS protein. In a primary screen, a plurality (e.g., a library) of compounds are contacted with cells that naturally or recombinantly express: (i) an IPS protein, fusion construct thereof, or a biologically active fragment of any of the foregoing; and (ii) a protein that is responsible for processing of the IPS protein in order to identify compounds that modulate the production, degradation, or post-translational modification of the IPS protein(s). If desired, compounds identified in the primary screen can then be assayed in a secondary screen against cells naturally or recombinantly expressing the specific IPS protein of interest. The ability of the candidate compound to modulate the production, degradation or post-translational modification of an IPS protein, can be determined by methods known to those of skill in the art, including without limitation, flow cytometry, a scintillation assay, immunoprecipitation and western blot analysis.

In another embodiment, agents that modulate (i.e., upregulate or downregulate) the expression of an IPS protein, are identified by contacting cells (e.g., cells of prokaryotic origin or eukaryotic origin) expressing the IPS protein with a candidate compound or a control compound (e.g., phosphate buffered saline (PBS)) and determining the expression of the IPS protein(s), or mRNA encoding the IPS protein(s). The level of expression of a selected IPS protein or mRNA in the presence of the candidate compound is compared to the level of expression of the IPS or mRNA in the absence of the candidate compound (e.g., in the presence of a control compound). The candidate compound can then be identified as a modulator of the expression of the IPS based on this comparison. For example, when expression of the IPS or mRNA is significantly greater in the presence of the candidate compound than in its absence, the candidate compound is identified as a stimulator of expression of the IPS or mRNA. Alternatively, when expression of the IPS or mRNA is significantly less in the presence of the candidate compound than in its absence, the candidate compound is identified as an inhibitor of the expression of the IPS or mRNA. The level of expression of an IPS protein or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of an IPS protein are identified by contacting a preparation containing the IPS protein, or cells (e.g., prokaryotic or eukaryotic cells) expressing the IPS protein with a test compound or a control compound and determining the ability of the test compound to modulate (e.g., stimulate or inhibit) the activity of the IPS protein. The activity of an IPS protein can be assessed by detecting induction of a cellular signal transduction pathway of the IPS (e.g., intracellular Ca2+, diacylglycerol, IP3, etc.), detecting catalytic or enzymatic activity of the target on a suitable substrate, detecting the induction of a reporter gene (e.g., a regulatory element that is responsive to an IPS and is operably linked to a nucleic acid encoding a detectable marker, e.g., luciferase), or detecting a cellular response, for example, cellular differentiation, or cell proliferation. Based on the present description, techniques known to those of skill in the art can be used for measuring these activities (see, e.g., U.S. Pat. No. 5,401,639, which is incorporated herein by reference). The candidate compound can then be identified as a modulator of the activity of an IPS protein by comparing the effects of the candidate compound to the control compound. Suitable control compounds include phosphate buffered saline (PBS) and normal saline (NS).

In another embodiment, agents that modulate (i.e., upregulate or downregulate) the expression, activity or both the expression and activity of an IPS are identified in an animal model. Examples of suitable animals include, but are not limited to, mice, rats, rabbits, monkeys, guinea pigs, dogs and cats. Preferably, the animal used represents a model of the disease of interest. In accordance with this embodiment, the test compound or a control compound is administered (e.g., orally, rectally or parenterally such as intraperitoneally or intravenously) to a suitable animal and the effect on the expression, activity or both expression and activity of the IPS protein is determined. In accordance with this embodiment, the test compound or a control compound is administered (e.g., orally, rectally or parenterally such as intraperitoneally or intravenously) to a suitable animal and the effect on the expression, activity or both expression and activity or both expression and activity of the IPS protein is determined. Changes in the expression of an IPS protein can be assessed by the methods outlined above.

In yet another embodiment, an IPS protein is used as a "bait protein" in a two-hybrid assay or three hybrid assay to identify other proteins, and/or RNA's, that bind to or interact with an IPS protein (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by the IPS protein of the invention as, for example, upstream or downstream elements of a signaling pathway involving the IPS protein of the invention.

Experimental Results

Rad23 proteins from yeast to humans contain $UbL^{R23}$ domains that bind the proteasome subunit Rpn10/S5a, and UBA domains that bind ubiquitin and ubiquitinated cellular proteins. Example 1 below shows that Rad23 can bind ubiquitinated cellular proteins. Significantly, the interaction required the UBA domains, since specific mutants failed to bind ubiquitinated cellular proteins, or test substrates in vivo. Because Rad23 mutants that lacked either UbL$^{R23}$ or functional UBA domains failed to suppress the defects of rad23Δrpn10Δ, the interactions with ubiquitinated proteins and the proteasome are both required for Rad23 function. It was also determined that high-level expression of Rad23 resulted in a dramatic increase in the levels of ubiquitinated proteins in the proteasome. This intriguing finding is the first evidence to reveal the interaction between ubiquitinated proteins and the proteasome in vivo. Furthermore, these findings suggest that Rad23 mediates the translocation of ubiquitinated proteins to Rpn10 that is present in the proteasome. Collectively, these results provide compelling support for a 'shuttle-factor hypothesis' wherein Rad23 and other proteins that contain UbL and UBA domains such as Dsk2 (Biggins et al. (1996) J. Cell Biol. 133:1331-1346) and Ddi1 (Clarke et al. (2001) Mol. Cell. Biol. 21:1997-2007), are novel regulators that translocate proteolytic substrates to the proteasome.

Rad23 was initially characterized as a DNA repair protein whose interaction with the repair factor Rad4 (XPC in humans) (Guzder et al. (1995) J. Biol. Chem. 270:12973-12976; van der Spek et al. (1996) supra) facilitated the assembly of repair proteins at sites of DNA lesions (Guzder et al. (1998) J. Biol. Chem. 273:31541-31546; Jansen et al. (1998) J. Biol. Chem. 273:33111-33114). The discovery of a ubiquitin-like (UbL) domain at the amino terminus of Rad23 suggested a potential proteolytic function, especially since full functionality was achieved when UbL$^{R23}$ was replaced by ubiquitin (Ub) (Watkins et al. (1993) Mol. Cell. Biol. 13:7757-7765). We reported previously that Rad23 interacted with catalytically active proteasomes through its UbL$^{R23}$ domain (Schauber et al. (1998) suprai). Loss of UbL$^{R23}$ in yeast Rad23 results in sensitivity to DNA damage, demonstrating that proteasome interaction is important during DNA repair. However, it is unclear if Rad23/proteasome interaction mediates a proteolytic event during NER (Gillette et al. (2001) Genes Dev. 15:1528-1539; Russell et al. (1999) Mol. Cell 3:687-695). While it is conceivable that Rad23/proteasome interaction involves a non-proteolytic function during DNA repair, several lines of evidence predict a role in proteolysis. Our studies, as well as other reports have shown that Rad23 can bind Ub (Bertolaet et al. (2001) supra; Chen et al. (2001) supra) regulate the assembly of substrate-linked multi-Ub chains (Ortolan et al. (2000) supra), and control the stability of proteins in vivo (Clarke et al. (2001) Mol. Cell. Biol. 21:1997-2007). Additionally, Rad23 was recently reported to bind multi-Ub chains in vitro (Wilkinson et al. (2001) Nat. Cell Biol. 3:939-943). Another study proposed that Rad23 might control the stability of Rad4 (Araki et al. (2001) J. Biol Chem. 276:18665-18672), which is intriguing because we showed previously that Rad4-HA could be co-purified with Rad23 and the 26S proteasome after several chromatography steps (Schauber et al. (1998) supra).

The expression of high levels of Rad23 resulted in the accumulation of ubiquitinated proteins in yeast cells. The UBA domains in Rad23 mediated an interaction with ubiquitinated cellular proteins in vivo, and mutants that were unable to bind ubiquitinated proteins displayed biochemical and physiological defects. The interaction between Rad23 and ubiquitinated proteins increased transiently after DNA damage, and these ubiquitinated proteins were converted to higher molecular-weight derivatives over time. In contrast, a Rad23 mutant that was unable to bind the proteasome ($^{\Delta UbL}$-rad23) formed a persistent interaction with ubiquitinated proteins, with no apparent increase in the formation of higher molecular-weight conjugates. One interpretation of this result is that, for some substrates, complete assembly of a multi-Ub chain might require an interaction with the proteasome.

Rad23 performs an overlapping role with Rpn10 (Lambertson et al. (1999) supra), a subunit in the proteasome that binds multi-Ub chains (van Nocker et al. (1996) Mol. Cell. Biol. 16:6020-6028). Rad23 mutants that are unable to bind ubiquitinated proteins failed to stabilize test substrates in vivo, or suppress the proteolytic and growth defects of rad23 rpn10. Consistent with previous in vitro studies, we discovered that Rpn10 interacted with ubiquitinated proteins in vivo and furthermore, formed a specific interaction with Rad23. Rad23 and Rpn10 contain different Ub-binding domains, and are likely to interact with structurally unique features in a multi-Ub chain. We previously showed that Rad23 could bind short, substrate-linked multi-Ub chains, and the results shown here indicate that Rad23 might also bind substrates that contain longer multi-Ub chains. The distal Ub moieties in a long multi-Ub chain are not tightly packed, and may resemble a short, substrate-linked multi-Ub chain (Cook et al. (1992) J. Biol. Chem. 267:16467-16471). In contrast, Rpn10 recognizes a hydrophobic patch that is created following the compaction of Ub moieties, in a long multi-Ub chain (Beal et al. (1998) Biochem. 37:2925-2934; Thrower et al. (2000) supra). The interaction between Rad23 and a multi-Ub chain could prevent dismantling by Ub-specific proteases, resulting in transient stabilization of the substrate, consistent with in vitro and in vivo data (Ortolan et al. (2000) supra). Subsequent delivery of the ubiquitinated substrate to Rpn10 in the proteasome could initiate degradation. These results are consistent with the idea that Rad23 and Rpn10 bind proteolytic substrates simultaneously, by recognizing different regions within a multi-Ub chain.

The overlapping genetic interactions between Rad23 and Rpn10 suggested that they might both influence the delivery of proteolytic substrates to the proteasome. Biochemical studies have shown that both Rpn10 and Rad23 can bind multi-Ub chains in vitro, ubiquitinated proteins in vivo and interact with the proteasome (Deveraux et al. (1994) supra; Glickman et al. (1998) Mol. Cell. Biol. 18:3149-3162; Schauber et al. (1998) supra). Consistent with these and other results (Hiyama et al. (1999) J. Biol. Chem. 274:28019-28025), we determined that Rad23 and Rpn10 interact. However, in contrast to the Hiyama et al. (1999) study (supra), we found that the UbL domain is not essential for Rad23/Rpn10 interaction, suggesting that a substrate-linked multi-Ub chain might bridge the interaction between these two proteins.

To examine the role of Rad23 and Rpn10 in the delivery of substrates to the proteasome we immunoprecipiated proteasomes from rpn10 and wildtype cells, using a subunit in the 20S core particle (Pre1-Flag). A low-level of ubiquitinated proteins was co-precipitated with proteasomes from a wild-type strain. In contrast, much lower levels of ubiquitinated proteins were detected in proteasomes that were isolated from rpn10, consistent with its interaction with multi-Ub chains. The levels of proteasome-associated ubiquitinated proteins increased dramatically when Rad23 was overexpressed, supporting the idea that it might deliver substrates to the proteasome. Significantly, overexpression of Rad23 in rpn10 resulted in the accumulation of very high levels of intracellular ubiquitinated proteins, although these ubiquitinated proteins could not be co-purified with the proteasome. A plausible interpretation of these results is that excess free Rad23 can interact with the proteasome and prevent access to substrate-bound Rad23. Consequently, ubiquitinated cellular proteins may fail to be delivered to the proteasome, while remaining sequestered in association with Rad23. In agreement with this conclusion, we found that much higher levels of ubiquitinated proteins accumulated when Rad23 was overexpressed in rpn10. Under normal conditions, Rad23/proteasome interaction may allow substrates to be transferred to Rpn10 to initiate further ubiquitination by proteasome-associated E3 (Xie et al. (2000) supra) and E2 factors Tongaonkar et al. (2000) Mol. Cell. Biol. 20:4691-4698). A failure to efficiently deliver ubiquitinated substrates to the proteasome may underlie the pleiotropic growth and proteolytic defects of rad23 rpn10.

Collectively, these findings provide the first evidence in vivo that the proteasome recognizes multi-ubiquitinated substrates. Our findings support important roles for both UbL$^{R23}$ and UBA domains in the translocation of proteolytic substrates to the proteasome. Since Rad23 performs overlapping roles with other proteins that contain both UbL and UBA domains (Ddi1 (Clarke et al. (2001) supra) and Dsk2 (Biggins et al. (1996) J. Cell Biol. 133:1331-1346), it is believed that this class of proteins encode novel regulators that deliver substrates to the proteasome. Our current understanding of Rad23 function can be represented by a simple model in which Rad23 (and other proteins that contain both UbL and UBA domains) are 'shuttle-factors' that translocate proteolytic substrates to the proteasome (FIG. 1). In agreement with the 'shuttle-factor' model we showed previously that Rad4 could be co-purified with Rad23 and the 26S proteasome. It has also been reported that the translocation of Png1 to the proteasome requires Rad23 (Suzuki et al. (2001) J. Biol. Chem. 275:21601-21607), although it is not clear if this protein is a substrate for degradation. Recent studies showed that Rad23 could control the abundance of the cell-cycle regulator Pds1 (Bertolaet et al. (2001) supra; (Clarke et al. (2001) supra). The failure to control Pds1 levels may account, in part, for the G2->M-phase transition defect of rad23 rpn10.

Example 2 describes further experiments validating the use of a specific ubiquitin-binding protein, recombinant human Rad23, to isolate and recover ubiquitinated proteins following a single affinity step.

EXAMPLES

The following examples are put forth so as to provide those of ordinary skill in the art with a complete disclosure and description of how to make and use the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Materials and Methods

Yeast strains and plasmids. A bar1Δ mutant was constructed using plasmid pJGSST1, in the haploid yeast strain JD47-13C (provided by Dr. J. Dohmen) (JD47-13C: MATa his3-Δ200 trp1-Δ63 lys2-801 ura3-52 leu2-112). The yeast RAD23 gene was deleted in JD47-13C using plasmid pDG28 (provided by Dr. R. D. Gietz). KMY1188 is an FOA-resistant derivative of this rad23Δ strain. Plasmids encoding Flag-Rad23, and the GST-set of Rad23 fusion proteins were described previously (see, for example, Araki et al. (2001) J. Biol. Chem. 276:18665-18672).

Protein and immunological methods. Pulse-chase and immunoblotting experiments were performed essentially as described previously (Ortolan et al. (2000) Nat. Cell Biol. 2:601-608 and Clarke et al. (2001) Mol. Cell. Biol. 21:1997-2007, both references specifically incorporated by reference).

Briefly, exponential-stage yeast cells (~30 ml volume at $A_{600}$=1) were washed and suspended in labeling buffer containing 250 µCi $^{35}$S-Met+$^{35}$S-Cys, and incubated for 5 min at 30° C. The incorporation of radioisotope was terminated by suspending the cells in medium containing 0.5 mg/ml cycloheximide and excess unlabeled methionine and cysteine. Aliquots were withdrawn at intervals and frozen in liquid N2. After all the time-points were collected, 0.5 mm acid-washed glass beads were added and the cells were lysed by vortexing. The incorporation of $^{35}$S label into TCA insoluble material was determined by scintillation counting, and equal amounts of protein were adjusted to equal volume and incubated with specific antibodies. Immunoprecipitations were typically carried out for 3 hours at 4° C., with constant rotation. The bound proteins were washed, resuspended in SDS-sample buffer, boiled and resolved in 10% SDS-containing polyacrylamide gels. The separated proteins were transferred to nitrocellulose using a Hoefer semi-dry transfer apparatus, and blocked with 5% milk powder. Antibodies against β-galactosidase were purchased from Promega Inc, (Madison, Wis.). Anti-Flag, anti-Ub and anti-GST antibodies were purchased from Sigma Chemical Co (St. Louis, Mo.). Antibodies against GST-Rad23 were prepared by Pocono Rabbit Co. For immunoblot detection, an enhanced chemiluminescence kit was purchased from Dupont/NEN. Protein-A SEPHAROSE® was purchased from Kendrick Laboratories (Cambridge, Mass.), and GST-SEPHAROSE® was purchased from Amersham/Pharmacia Biotech (Piscataway, N.J.). The results were quantitated using Kodak 1D-3.5 software.

Cell-cycle analysis. The growth of yeast bar1-1 mutant cells was arrested by adding 10 ng/ml alpha-factor (Sigma). The efficiency of arrest was determined microscopically, and after greater than 95% of the cells had arrested in G1 they were resuspended in fresh medium lacking alpha-factor to resume mitotic growth. An aliquot of the culture was withdrawn immediately after resuspension and suspended for 5 min in labeling buffer containing 200 µCi $^{35}$S-methionine+$^{35}$S-cysteine. Further incorporation of $^{35}$S-label was terminated by the addition of cycloheximide, and the cells incubated for further 60 min (chase). Equal volume aliquots were removed during the chase after 0, 10 and 60 minutes, and frozen in liquid N2. Similar pulse-chase experiments were performed at 30 min intervals, five additional times during the cell-cycle. Equal amounts of trichloroacetic acid (TCA) insoluble material were reacted with antibodies against native Rad23 and the precipitated proteins separated by SDS/PAGE, transferred to nitrocellulose and exposed to X-ray film. The same filter was subsequently incubated with antibodies against ubiquitin, and detected by enhanced chemiluminescence.

Construction of RAD23 mutations. DNA oligonucleotides were synthesized to delete UBA$^1$, or generate mutations in UBA$^1$ and UBA$^2$ domains of yeast RAD23. Oligonucleotides complementary to the 5' and 3' ends of the RAD23 gene contained EcoR1 and Kpn1 DNA restriction sites for cloning into a Flag-epitope containing vector for expression in yeast. However, for expression of the same RAD23 alleles in E. coli we amplified the DNA with oligonucleotides that contained Nco1 and BamnH1 DNA restriction sites on the 5' and 3' ends and cloned the DNA into pET11d (Novogen, Inc). The oligonucleotides used for generating the UBA mutations are shown below, and the mutated genes were subjected to DNA sequencing for confirmation. The primers used for generating a deletion of UBA$^1$ was described previously (Ortolan et al. (2000) supra): # 461: 5'-GAATATGCACTGATGGGTATTC-CAG-3' (SEQ ID NO:1); # 462: 5'-GAATACCCATCAGTG-CATATTCCACCGC-3' (SEQ ID NO:2); # 470: 5'-GCG-GATCCTCAGTCGGCATGATCGCTGAATGCATATTT-GCTGCAGC-3' (SEQ ID NO:3).

Results. Rad23 binds ubiquitinated proteins. High-level expression of Rad23 led to the accumulation of ubiquitinated proteins in yeast cells. A control strain that was grown in similar conditions, or overexpressed Rpn10, did not display this effect. Previous studies showed that Rad23 could bind free ubiquitin (Ub) (Bertolaet et al. (2001) Nat. Struct. Biol. 8:417-422; Chen et al. (2001) EMBO Rep 2), although it was anticipated that its natural targets would represent ubiquitinated proteins. The accumulation of high molecular weight ubiquitinated proteins led us to determine if they were bound to Rad23.

A set of glutathione S-transferase (GST)-Rad23 fusion proteins were purified from yeast cells (Schauber et al. (1998) Nature 391:715-718) to characterize the interaction with ubiquitinated proteins. Equal amounts of extract were incubated with glutathione- SEPHAROSE® and the proteins bound to the GST fusion proteins were examined in an immunoblot with antibodies against Ub. Both full-length Rad23, as well as a mutant that lacked the N-terminal ubiquitin-like domain ($^{\Delta UbL}$rad23), formed a strong interaction with ubiquitinated proteins. In contrast, neither GST nor the UbL$^{R23}$ domain alone formed a detectable interaction with ubiquitinated proteins. Although UbL$^{R23}$ can interact with the proteasome (which binds ubiquitinated proteins ), these results suggest that ubiquitinated substrates are normally not detected in association with the proteasome because they are rapidly degraded (results not shown).

UBA domains in Rad23 mediate the interaction with ubiquitinated proteins. The ubiquitin-associated domains (UBA) (Hofman et al. (1996) Trends Bio. Sci. 21:172-173) in Rad23 (van der Spek et al. (1996) Genomics 31:20-27) and other proteins bind Ub (Bertolaet et al. (2001) supra; Chen et al. (2001) supra), although it was not known if they could bind ubiquitinated proteins in vivo. To examine this possibility we generated a set of Rad23 mutants that were based on studies described previously (Bertolaet et al. (2001). We constructed Rad23 mutants that lacked UBA$^1$, or contained single amino acid substitutions in each UBA domain to prevent their interaction with Ub. Each derivative was expressed with an amino-terminal Flag epitope to facilitate rapid purification from yeast cells. Flag-Rad23 can functionally replace the native protein. In agreement with the results above, ubiquitinated proteins were efficiently co-purified with Flag-Rad23. However, a single amino acid substitution in UBA$^1$ (L183A; rad23$^{uba1}$) caused an 80% reduction in the amount of ubiquitinated protein that was recovered. In contrast, a similar mutation in UBA$^2$ (L392A; rad23$^{uba2}$) decreased the binding by only 20%, consistent with its weaker interaction with Ub that was previously described (Bertolaet et al. (2001) supra; Chen et al. (2001) supra). A Rad23 mutant that contained mutations in both UBA domains (rad23$^{uba1,uba2}$) was completely defective, and the interaction with ubiquitinated proteins was reduced to ~1%, compared to the wildtype protein. In contrast to the single amino acid substitution in UBA$^1$ (rad23$^{uba1}$), deletion of the entire domain (rad23$^{\Delta uba1}$; removal of residues 141-190) caused a very severe defect, and the interaction with ubiquitinated proteins was reduced to ~1%, despite the presence of intact UBA$^2$. Since the UBA domains in Rad23 have been reported to participate in the formation of homodimers (Bertolaet et al. (2001a) J. Mol. Biol. 313:955-963; Bertoleat et al. (2001) supra), it is possible that they contribute to the conformational integrity of the protein, and a deletion could cause significant structural perturbations. Removal of UbL$^{R23}$ ($^{\Delta UbL}$rad23), which is believed to form an independently folded domain (Schauber et al. (1998) supra, and our unpublished studies), did not affect the interaction with ubiquitinated proteins. The same filter was also incubated with antibodies against Cim5/Rpt1, one of the six ATPases present in the 19S regulatory particle of the proteasome (Glickman et al. (1998) Mol. Cell. Biol. 18:3149-3162). With the exception of $^{\Delta UbL}$rad23, all the other Rad23 derivatives contained UbL$^{R23}$, and were able to bind the proteasome. The human counterparts of Rad23 (hHR23-A and hHR23-B) can also bind the proteasome, and block the assembly of substrate-linked multi-Ub chains (Ortolan et al. (2000) Nat. Cell Biol. 2:601-608). To further assess their similarity to the yeast protein we expressed GST-hHR23-B in yeast and found that it could bind ubiquitinated proteins in vivo. Since the sequence and structure of Ub are virtually identical in yeast and humans, these results suggest that the UBA domains in Rad23 proteins play an evolutionarily conserved role in binding ubiquitinated proteins. We also investigated if Rpn10 could bind ubiquitinated proteins in vivo, since this protein and its human counterpart S5a have been shown to bind unlinked multi-Ub chain in vitro (Deveraux et al. (1994) J. Biol. Chem. 269:7059-7061; van Nocker et al. (1996) Mol. Cell. Biol. 16:6020-6028). In agreement with the in vitro results, we found that Flag-Rpn10 could bind ubiquitinated proteins in yeast cells.

UBA mutants fail to stabilize substrates in vivo. We next investigated if mutations in the UBA domains had an effect on the biochemical properties of Rad23. We first measured the binding between Flag-Rad23 and the proteolytic substrates Arg-βgal and Ub-Pro-βgal, which are ubiquitinated and degraded by the proteasome (2; Varshavsky (1997) Trends Biochem. Sci. 22:383-387). Flag-Rad23 could co-immunoprecipitate ubiquitinated Ub-Pro-βgal and Arg-βgal, but not Met-βgal, which is not a target for degradation. In contrast, Rad23 derivatives that contained mutations in the UBA domains were impaired to varying degrees in binding these substrates, in proportion to their ability to interact with ubiquitinated cellular proteins. In the next experiment, the cellular levels of Flag-rad23$^{uba2}$ and Flag-rad23$^{uba1uba2}$ mutant proteins were ~3-fold higher than Flag-Rad23, accounting for the higher levels of bound substrates. Flag-rad23$^{\Delta uba1}$ and Flag-rad23$^{uba1uba2}$ interacted poorly with Arg-βgal and Ub-Pro-βgal, while Flag-rad23$^{uba2}$ showed significant interaction with both proteolytic substrates.

The overexpression of Rad23 causes stabilization of proteolytic substrates in yeast cells. We therefore measured protein stability by pulse-chase methods to confirm that the failure of Flag-rad23$^{uba1uba2}$ to bind ubiquitinated proteins would result in constitutive degradation of Ub-Pro-βgal. As expected, Ub-Pro-βgal was efficiently ubiquitinated and degraded in a wild type cell ($t_{1/2}$~7 min) (results not shown), while overexpression of Flag-Rad23 prevented the expansion of multi-Ub chains on Ub-Pro-βgal, resulting in strong stabilization ($t_{1/2}$>100 min). In contrast to Flag-Rad23, Flag-rad23$^{uba1uba2}$ did not inhibit the multi-ubiquitination and degradation of Ub-Pro-βgal ($t_{1/2}$~10 min), demonstrating that the interaction between UBA domains in Rad23 and Ub moieties on a substrate is important for controlling protein stability.

Rad23 forms transient interactions with ubiquitinated proteins. Previous studies led us to propose that Rad23 might play a role in the delivery of proteolytic substrates to the proteasome (Lambertson et al. (1999) Genetics 153:69-79; Schauber et al. (1998) supra). To examine this idea further we measured the interaction between Rad23 and ubiquitinated proteins in a time-course assay. The growth of yeast cells was inhibited in G1-phase by the addition of alpha mating-factor to the medium (Madura et al. (1990) Nuc. Acids Res. 18:4737-4742). The culture was released from G1 arrest, and allowed to grow synchronously for approximately two generations, during which we conducted pulse-chase analysis at 30 min intervals, to measure the interaction between ubiquitinated proteins and native Rad23 protein. We found that Rad23 formed an association with high molecular weight, $^{35}$S-labeled material throughout the cell-cycle. As noted previously, native Rad23 is stable (Watkins et al. (1993) Mol. Cell. Biol. 13:7757-7765), despite its interaction with the proteasome (Schauber et al. (1998) supra). When the same filter was incubated with anti-Ub antibodies we detected a strong reaction against high molecular-weight species, consistent with the hypothesis that Rad23 binds cellular proteins that are ubiquitinated. Significantly, the interaction between Rad23 and ubiquitinated proteins decreased rapidly during the chase. We speculate that this decrease reflects proteasome-mediated degradation of the ubiquitinated proteins that are bound to Rad23.

The interaction between Rad23 and ubiquitinated proteins increased following DNA damage. A recent report indicated that the UBA domains are not required for the DNA repair-specific functions of Rad23 (Bertolaet et al. (2001) supra). It was also proposed that during NER the interaction between Rad23 and the proteasome does not involve proteolysis (Gillette et al. (2001) Genes Dev. 15:1528-1539; Russell et al. (1999) Mol. Cell 3:687-695). However, genetic results showed that Rad23 plays an overlapping role with Rpn10 (Lambertson et al. (1999) Genetics 153:69-79), a proteasome-associated multi-Ub chain-binding factor (van Nocker et al. (1996) Mol. Cell. Biol. 16:6020-6028). Furthermore, the UbL domain in human Rad23 could bind S5a, a human counterpart of Rpn10. Recent studies have shown that Rad23 can bind Ub (Bertolaet et al. (2001) supra; Chen et al. (2001) supra; Wilkinson et al. (2001) Nat. Cell Biol. 3:939-943, interact with ubiquitinated proteins, and regulate the assembly of substrate-linked multi-Ub chains (Ortolan et al. (2000) Nat. Cell Biol. 2:601-608). Since the removal of UbLR$^3$ from Rad23 prevents interaction with the proteasome (Schauber et al. (1998) supra) and causes sensitivity to DNA damage (Watkins et al. (1993) Mol. Cell. Biol. 13:7757-7765), it is possible that Rad23 performs a proteolytic role in its diverse biological activities.

To explore the link between NER and proteolysis, we examined Rad23 interaction with ubiquitinated proteins following DNA damage. An actively growing culture of yeast cells was exposed to the UV mimetic agent 4-nitrosoquinoline oxide (4-NQO), or to alpha mating-factor. Protein extracts were prepared and Flag-Rad23 was precipitated. The proteins were separated by SDS/PAGE, transferred to nitrocellulose and incubated with antibodies against Ub. An equivalent amount of ubiquitinated proteins was bound to Flag-Rad23 in untreated and alpha-factor treated cells (results not shown). In contrast, the interaction between Rad23 and ubiquitinated proteins increased ~2-fold after treatment with 4-NQO. The quantitation of these results was adjusted for the amount of Flag-Rad23 that was precipitated. To further characterize the effect of DNA damage we compared the binding between ubiquitinated proteins and either Flag-Rad23 or Flag-$^{\Delta UbL}$rad23, a mutant that causes a defect in DNA repair (Watkins et al. (1993) supra). Yeast cells that expressed either Flag-Rad23 or Flag-$^{\Delta UbL}$rad23 were exposed to 4-NQO for 60 min and then resuspended in medium lacking this DNA damaging agent. Aliquots of the culture were withdrawn after 0, 10, 30 and 60 min, and protein extracts prepared. Equal amounts of protein were incubated with Flag-agarose and the ubiquitinated proteins that were bound to Rad23 were detected by immunoblotting. We found that the overall amount of ubiquitinated proteins that was bound to Rad23 decreased over the 60 min duration. Intriguingly, we observed that the ubiquitinated species that were bound to Flag-Rad23 were re-distributed towards higher molecular weight forms during the course of the incubation. The interaction between Rad23 and the proteasome was unaffected, as revealed by the precipitation of Cim5/Rpt1. In contrast to these results, the ubiquitinated species that were bound to Flag-$^{\Delta UbL}$rad23 were more heterogenous in size, and we did not observe a significant conversion towards higher molecular weight derivatives. As expected, Flag-$^{\Delta UbL}$rad23 did not form an appreciable interaction with the proteasome. Two panels (D and G, which were the same filters as B and E), were probed with anti-Rad23 antibodies, and the positions of Flag-Rad23 and Flag-$^{\Delta UbL}$rad23 are indicated. Since substrate-ubiquitinating factors are present in the proteasome (Tongaonkar et al. (2000) Mol. Cell. Biol. 20:4691-4698; Verma et al. (2000) Mol. Biol. Cell 11:3425-3439; Xie et al. (2000) Proc. Natl. Acad. Sci. (USA). 97:2497-2502), these findings raise the possibility that the complete ubiquitination of proteolytic substrates might occur after their translocation to the proteasome by Rad23.

UBA mutants fail to suppress the growth and proteolytic defects of Rad23Δrpn10Δ. The rad23Δrpn10Δ double mutant is unable to grow in the presence of the amino acid analog canavanine, or at low temperature (Lambertson et al. (1999) Genetics 153:69-79). rad23Δrpn10Δ also displays proteolytic defects and a delay during the $G_2$ phase of the cell cycle. These pleiotropic phenotypes are completely suppressed following transformation with a plasmid that encodes either Rad23 or Rpn10. To determine if Rad23/proteasome interaction played a role in this suppression, we expressed $^{\Delta UbL}$rad23 in rad23Δrpn10Δ and found that it was unable to alleviate any of the defects, underscoring the importance of proteasome interaction for Rad23 function. Here we investigated if the interaction between Rad23 and ubiquitinated proteins was also required for suppressing the defects of rad23Δrpn10Δ. We expressed Flag-rad23$^{uba1uba2}$ in rad23Δrpn10Δ and found that this mutant failed to restore growth at low temperature, or in the presence of the amino acid analog canavanine (results now shown). A mutation in UBA$^2$ enabled Flag-rad23$^{uba2}$ to grow well at 30° C. and 23° C., but not at 13° C., consistent with its moderate interaction with ubiquitinated proteins. In contrast, Flag-rad23$^{uba1uba2}$ was as growth impaired as rad23Δrn10Δ at 30° C., 23° C. and 13° C., reflecting its inability to bind ubiquitinated cellular proteins. Interestingly, both mutant proteins failed to permit growth in medium containing canavanine, indicating that the generation of damaged proteins by amino acid analogs requires fully functional Rad23 protein. Taken together, our genetic and biochemical results reveal a correspondence between the biological activity of Rad23, and the efficiency of interaction with ubiquitinated proteins.

Rad23 binds Rpn10 and stimulates the interaction between ubiquitinated proteins and the proteasome. Rad23 and Rpn10 can bind ubiquitinated proteins through distinct interacting domains (see, for example, Bertoleat et al. (2001) supra) suggesting that they recognize structurally different features in a multi-Ub chain. In support of this argument, we note that a proteolytic substrate that contains only one or two Ub moieties is a very poor target for Rpn10 (Piotrowski et al. (1997) J. Biol. Chem. 272; Thrower et al. (2000) EMBO J. 19:94-102), although it can be readily co-immunoprecipitated with Rad23 (Ortolan et al. (2000) supra). Furthermore, Rpn10 does not show appreciable interaction with mono-Ub, unlike Rad23. Consequently, it is possible that Rad23 and Rpn10 bind simultaneously to multi-Ub chains on substrates.

Although the function of Rad23 remains to be clearly elucidated, we speculated that it might regulate the stability of proteolytic substrates by controlling their delivery to the proteasome (Lambertson et al. (1999) supra; Ortolan et al. (2000) supra; Schauber et al. (1998) supra). Based on the genetic interaction between Rad23 and Rpn10, it was likely that both proteins participated in this activity. An attractive model for Rad23 function would posit that it binds ubiquitinated proteins through the two UBA domains, while a subsequent interaction with the proteasome (involving the $UbL^{R23}$ domain), would permit the transfer of the proteolytic substrate to Rpn10. One might predict that the expansion of a multi-Ub chain would be inhibited while the protein was bound to Rad23, consistent with both in vitro and in vivo results. The presence of two UBA domains in Rad23 provides a mechanistic basis for the interaction with proteolytic substrates that are ligated to Ub.

It was previously reported that the UbL domain in human Rad23 could bind S5a (Hiyama et al. (1999) J. Biol. Chem. 274:28019-28025), the counterpart of yeast Rpn10. Although Rad23 can bind the proteasome in a strain that lacks Rpn10 (Lambertson et al. (1999) supra), it was possible that it interacted with multiple subunits in the proteasome, including Rpn10. Furthermore, since mutations in both the UbL and UBA domains of Rad23 resulted in a failure to suppress the defects of rad23Δ rpn10Δ we determined if Rad23 interacted with Flag-Rpn10. We expressed GST, GST-Rad23, $GST-^{\Delta UbL}rad23$ and $GST-UbL^{R23}$ in a yeast strain that also contained Flag-Rpn10. Equal amounts of protein extract were applied to glutathione-SEPHAROSE® to precipitate the GST-fusion proteins, or Flag-agarose to precipitate Flag-Rpn10. We found that Flag-Rpn10 co-precipitated GST-Rad23, and in the reciprocal experiment GST-Rad23 co-purified Flag-Rpn10 (results not shown). Interestingly, $GST-^{\Delta UbL}rad23$ also formed an efficient interaction with Flag-Rpn10. Because this Rad23 mutant is unable to bind the proteasome, it is possible that Rad23 and Rpn10 can bind ubiquitinated substrates prior to interaction with the proteasome. However, further study will be required to resolve this interesting finding. Very low levels of $GST-UbL^{R23}$ were co-precipitated with Flag-Rpn10, although high amounts were detected in the reciprocal experiment. It is unclear if Rpn10 interacts directly with $UbL^{R23}$, or if its co-precipitation with Flag-Rpn10 occurs because both proteins bind the proteasome. Human hHR23-B also interacted with Flag-Rpn10, which was anticipated because we determined that it could interact with multi-Ub chains. The interaction between yeast Rad23 and Rpn10 supports our genetic studies, which revealed overlapping functions for these two proteins (Lambertson et al. (1999) supra).

To characterize the significance of Rad23/Rpn10 interaction, we investigated if the targeting of ubiquitinated proteins to the proteasome was affected. We expressed an epitope-tagged proteasome subunit (Pre1-Flag) in wildtype and rpn10Δ cells, as well as a plasmid that could express RAD23 at high levels from the galactose-inducible GAL1 promoter. Proteasomes were immunopurified on Flag-agarose, and the proteins separated by SDS/PAGE, transferred to nitrocellulose and incubated with anti-Ub antibodies. Low levels of ubiquitinated proteins were associated with proteasomes that were immunoprecipitated from wildtype cells (results not shown). In contrast, much lower levels of ubiquitinated cellular proteins were bound to proteasomes that were purified from rpn10Δ, which may be due to the absence of this multi-Ub chain-binding protein. Alternatively, proteasomes have been reported to be unstable in rpn10Δ (Glickman et al. (1998) Cell 94:615-624), which could result in poor recovery of ubiquitinated substrates. Significantly higher amounts of ubiquitinated proteins were precipitated with the proteasome when Rad23 was overexpressed in a wildtype cell. Remarkably, a similar increase was not detected when Rad23 was overexpressed in a strain that lacked Rpn10. This result is all the more striking, given that the high expression of Rad23 in rpn10Δ resulted in dramatically increased amounts of intracellular ubiquitinated proteins. Collectively, our results support the hypothesis that Rad23 binds ubiquitinated substrates and regulates their delivery to Rpn10 in the proteasome.

Example 2

Rad23 Can Bind Ubiquitinated Proteins In Vivo

Human hHR23-B was expressed as a fusion to glutathione S-transferase. Protein extracts were applied to glutathione-SEPHAROSE®, and the proteins bound to GST-hHR23-B were examined in an immunoblot. A significant reaction, that extended from ~20 kDa to greater than 200 kDa was detected against anti-Ub antibodies (results not shown). These proteins were bound to hHR23-B very tightly, and could only be dissociated by treatment with SDS. No anti-Ub cross-reacting material was detected in a second lane containing only GST. These data demonstrate that human Rad23 binds ubiquitinated proteins that can be recovered following a single affinity step.

What is claimed is:

1. A method for establishing an expression profile of purified ubiquitinated proteins which are targeted for degradation by a ubiquitin pathway for a disease or pathological biological sample comprising ubiquitinated proteins, wherein the biological sample is a tissue, a cell, a peripheral blood sample, a body fluid sample, a tissue biopsy sample, protein extract isolated from the tissue or cell, or a stool sample, comprising
   (a) contacting the biological sample comprising ubiquitinated proteins which are targeted for degradation by the ubiquitin pathway with a ubiquitin-specific-binding protein attached to an affinity matrix, wherein the ubiquitin-specific-binding protein consists of ubiquitin-associated domain 1 (UBAI) of Rad23, such that ubiquitinated proteins which are targeted for degradation by the ubiquitin pathway bind to the ubiquitin-specific-binding protein;
   (b) separating ubiquitinated proteins that bound the ubiquitin-specific-binding protein in step (a) and which are targeted for degradation by the ubiquitin pathway from affinity matrix supernatant comprising proteins of the biological sample that did not bind to the ubiquitin-specific-binding protein in step (a);
   (c) contacting the affinity matrix supernatant from step (b) with a ubiquitin-specific-bindingprotein attached to a new affinity matrix, wherein the ubiquitin-specific-binding protein also consists of ubiquitin-associated domain 1 (UBAI) of Rad23, such that ubiquitinated proteins which are targeted for degradation by the ubiquitin pathway bind to the ubiquitin-specific-bindingprotein;
   (d) isolating ubiquitinated proteins which are targeted for degradation by the ubiquitin pathway by isolating ubiquitinated proteins that bound to the ubiquitin-specific-binding protein in step (c); and
   (e) analyzing the isolated ubiquitinated proteins of step (d) which are targeted for degradation by the ubiquitin pathway by comparing pattern and abundance of said ubiquitinated proteins of step (d) from the disease or pathological biological sample with pattern and abundance of ubiquitinated proteins of a control sample to establish the expression profile of ubiquitinated proteins which are targeted for degradation by the ubiquitin pathway for the biological sample.

2. The method of claim 1, further comprising release of the bound ubiquitinated proteins of step (d) from the affinity matrix by a de-ubiquitination reaction to generate isolated de-ubiquitinated proteins.

3. The method of claim 2, wherein the analyzing step (e) is conducted by subjecting the isolated de-ubiquitinated proteins to high-resolution 2-dimensional (2D) gel electrophoresis.

4. The method of claim 3, wherein 2D gel electrophoresis is followed by visualization of the isolated de-ubiquitinated proteins.

5. The method of claim 4, wherein visualization is achieved with silver nitrate staining.

6. The method of claim 1, further comprising release of the bound ubiquitinated proteins of step (d) from the affinity matrix by exposure to high salt conditions, detergent, or enzymatic reaction.

7. The method of claim 6, wherein the bound ubiquitinated proteins of step (d) are released from the affinity matrix by exposure to ubiquitin-isopeptidase.

* * * * *

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
gaatatgcac tgatgggtat tccag                                          25
```

```
<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
gaatacccat cagtgcatat tccaccgc                                          28

<210> SEQ ID NO 3
<211> LENGTH: 47
<212> TYPE: DNA
<213> ORGANISM: Artificial Sequence
<220> FEATURE:
<223> OTHER INFORMATION: primer

<400> SEQUENCE: 3
gcggatcctc agtcggcatg atcgctgaat gcgatatttg ctgcagc                     47
```